(12) United States Patent
Van Den Heuvel

(10) Patent No.: US 11,128,967 B2
(45) Date of Patent: Sep. 21, 2021

(54) TRANSDUCER PLACEMENT FOR GROWTH ACCOMMODATION

(71) Applicant: Koen Erik Van Den Heuvel, Mechelen (BE)

(72) Inventor: Koen Erik Van Den Heuvel, Mechelen (BE)

(73) Assignee: Cochlear Limited, Macquarie University (AU)

( * ) Notice: Subject to any disclaimer, the term of this patent is extended or adjusted under 35 U.S.C. 154(b) by 806 days.

(21) Appl. No.: 15/440,928

(22) Filed: Feb. 23, 2017

(65) Prior Publication Data
US 2018/0235812 A1     Aug. 23, 2018

(51) Int. Cl.
*H04R 25/00*     (2006.01)

(52) U.S. Cl.
CPC .... *H04R 25/606* (2013.01); *A61F 2220/0008* (2013.01); *H04R 2460/13* (2013.01)

(58) Field of Classification Search
CPC .................................................... H04R 25/606
See application file for complete search history.

(56) References Cited

U.S. PATENT DOCUMENTS

| | | | |
|---|---|---|---|
| 6,325,755 B1 | 12/2001 | Bushek et al. | |
| 8,216,123 B2 | 7/2012 | Cho et al. | |
| 2002/0032363 A1* | 3/2002 | Kroll | H04R 25/456 |
| | | | 600/25 |
| 2002/0035308 A1* | 3/2002 | Brillhart | H04R 25/456 |
| | | | 600/25 |
| 2009/0124849 A1 | 5/2009 | Pergola | |
| 2011/0029031 A1 | 2/2011 | Parker | |
| 2011/0112355 A1 | 5/2011 | Van den Heuvel | |
| 2012/0136197 A1 | 5/2012 | Van Gerwen | |
| 2012/0157815 A1 | 6/2012 | Pau et al. | |
| 2013/0116497 A1 | 5/2013 | Vermeiren et al. | |
| 2013/0165737 A1 | 6/2013 | Van den Heuvel | |
| 2013/0225912 A1 | 8/2013 | Leigh | |
| 2014/0094646 A1 | 4/2014 | Leigh et al. | |
| 2018/0376262 A1 | 12/2018 | Badih et al. | |

FOREIGN PATENT DOCUMENTS

| | | |
|---|---|---|
| CN | 103429297 A | 12/2013 |
| CN | 108713325 A | 10/2018 |
| KR | 100859979 B1 | 9/2008 |
| WO | 9963785 A3 | 3/2003 |

OTHER PUBLICATIONS

International Search Report and Written Opinion for PCT/IB2018/050355, dated May 2, 2018.
Office Action for CN Application No. 201880021899.1, dated Sep. 22, 2020.

\* cited by examiner

*Primary Examiner* — Christine H Matthews
(74) *Attorney, Agent, or Firm* — Pilloff Passino & Cosenza LLP; Martin J. Cosenza

(57) ABSTRACT

An implantable apparatus, including an implantable transducer fixation mechanism, the fixation mechanism being configured to receive an implantable transducer, wherein the fixation mechanism is configured to be fixed to a wall of the middle ear cavity of the recipient, and the fixation mechanism is configured to locate the transducer at least partially outside the middle ear cavity.

30 Claims, 34 Drawing Sheets

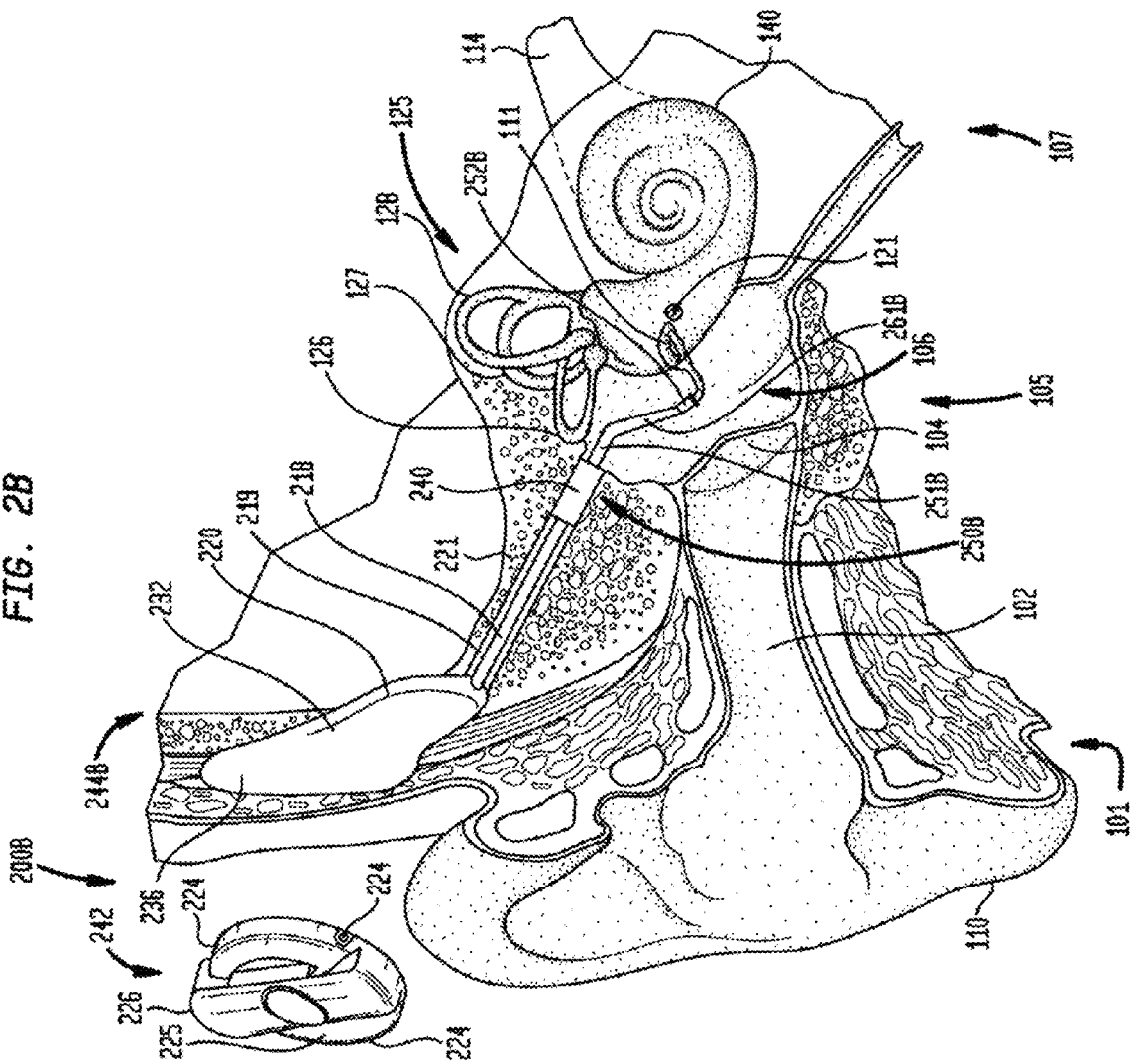

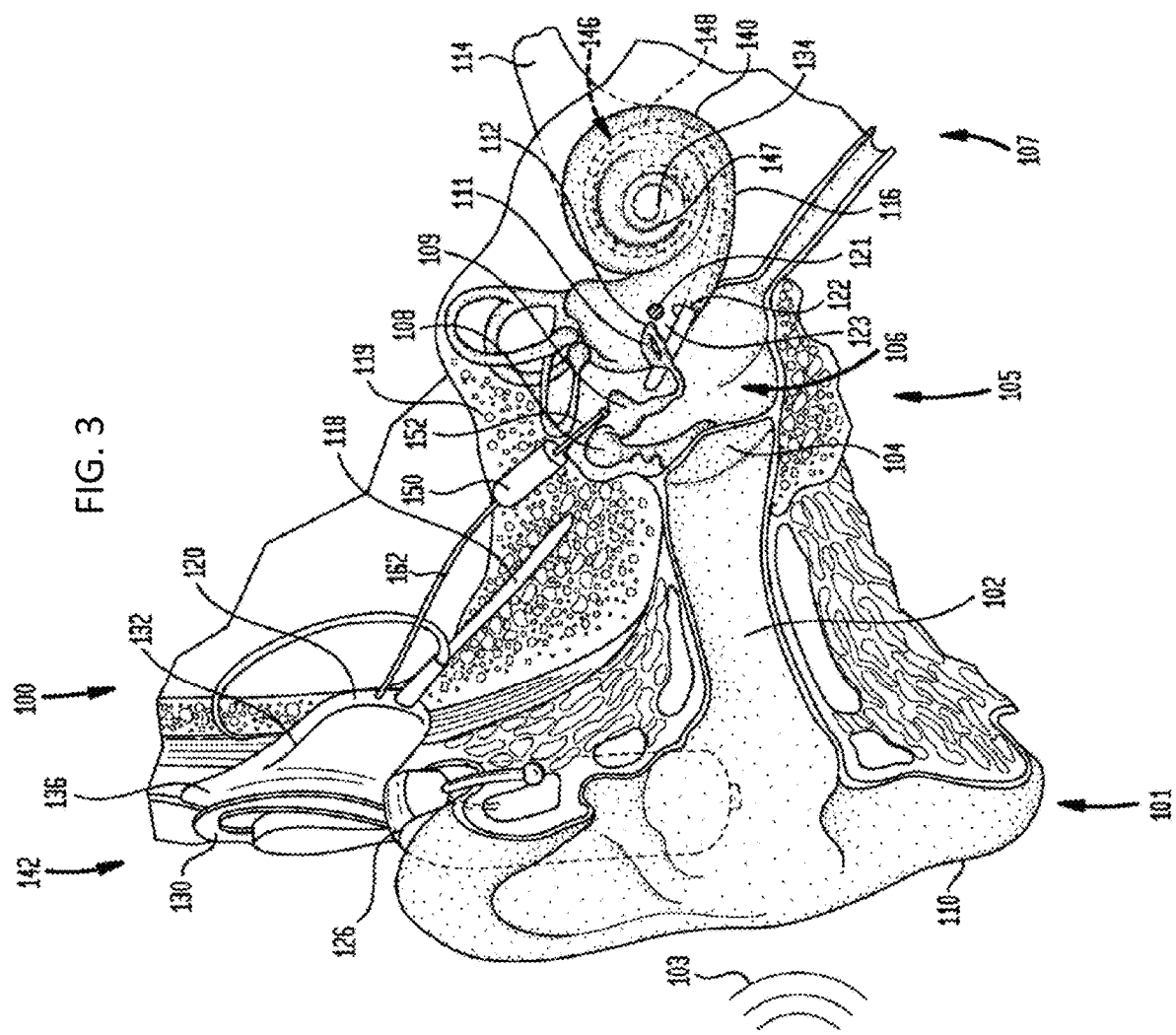

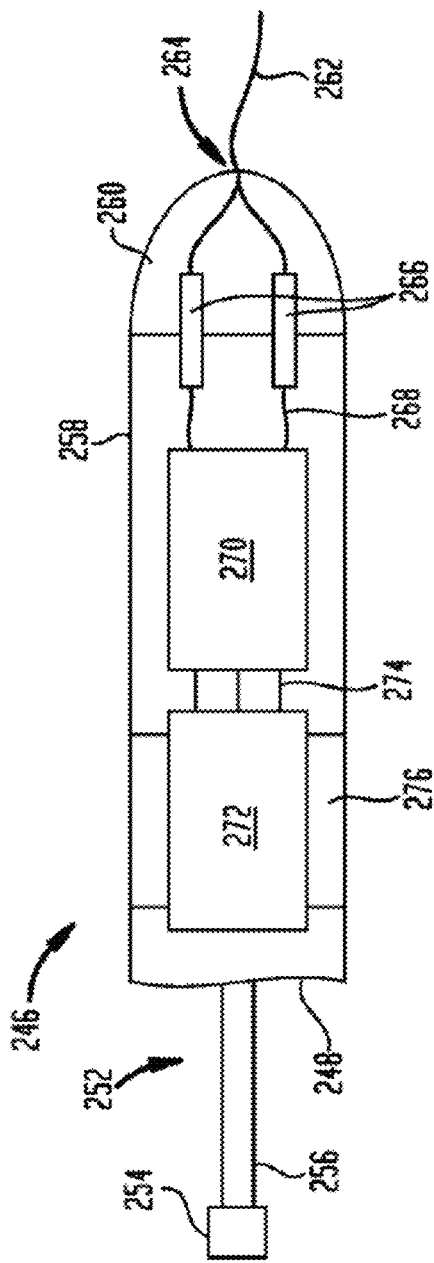

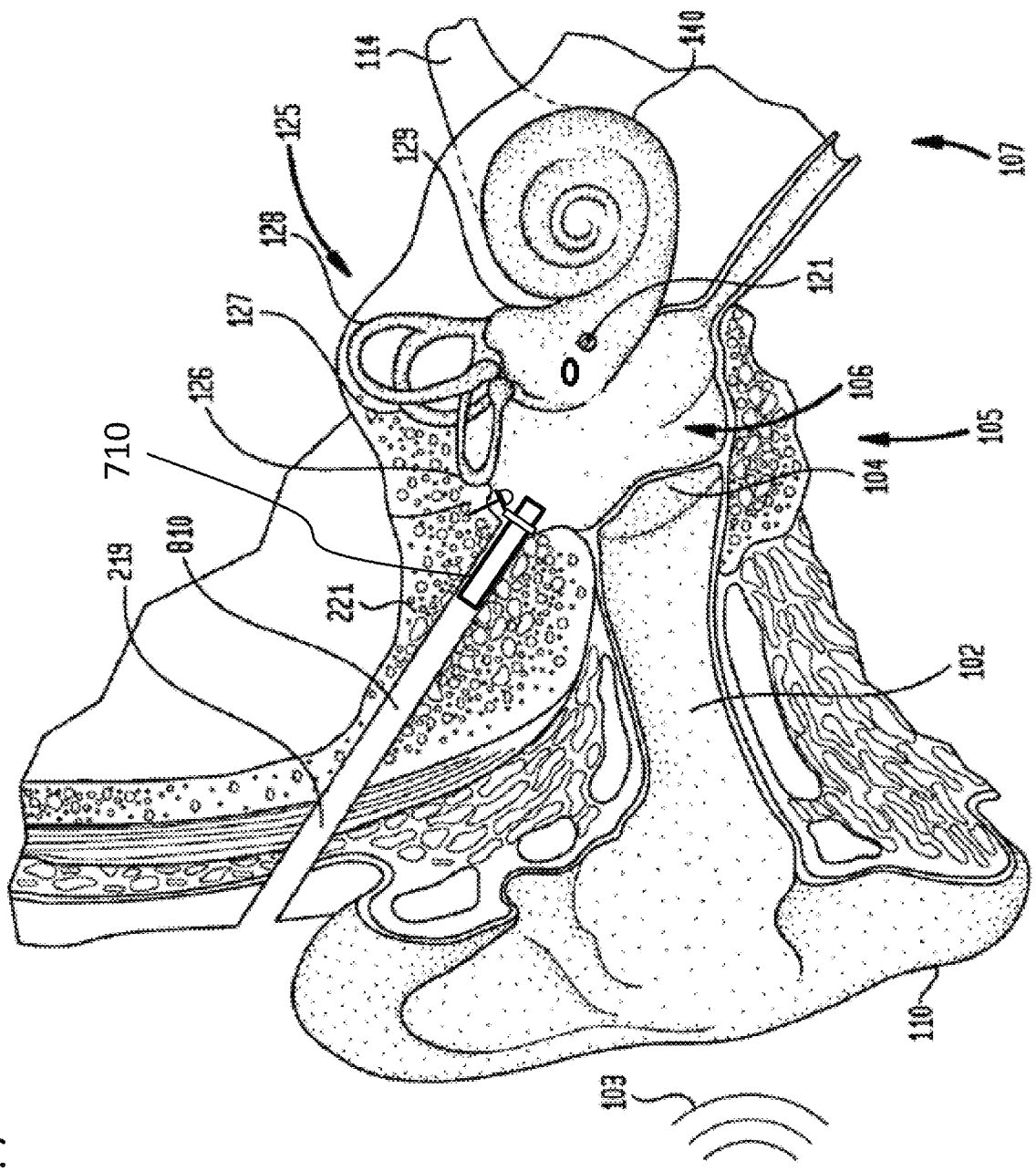

TRANSDUCER PLACEMENT FOR GROWTH ACCOMMODATION

BACKGROUND

Hearing loss is generally of two types, conductive and sensorineural. Sensorineural hearing loss is due to the absence or destruction of the cochlear hair cells which transduce sound into nerve impulses. Various hearing prostheses have been developed to provide individuals suffering from sensorineural hearing loss with the ability to perceive sound. For example, cochlear implants have an electrode assembly which is implanted in the cochlea. In operation, electrical stimuli are delivered to the auditory nerve via the electrode assembly, thereby bypassing the inoperative hair cells to cause a hearing percept.

Conductive hearing loss occurs when the natural mechanical pathways that provide sound in the form of mechanical energy to cochlea are impeded, for example, by damage to the ossicular chain or ear canal. For a variety of reasons, such individuals are typically not candidates for a cochlear implant. Rather, individuals suffering from conductive hearing loss typically receive an acoustic hearing aid. Hearing aids rely on principles of air conduction to transmit acoustic signals to the cochlea. In particular, hearing aids amplify received sound and transmit the amplified sound into the ear canal. This amplified sound reaches the cochlea in the form of mechanical energy, causing motion of the perilymph and stimulation of the auditory nerve.

Not all individuals suffering from conductive hearing loss are able to derive suitable benefit from hearing aids. For example, some individuals are prone to chronic inflammation or infection of the ear canal. Other individuals have malformed or absent outer ear and/or ear canals resulting from various scenarios.

For these and other individuals, another type of hearing prosthesis has been developed in recent years. This hearing prosthesis, commonly referred to as a middle ear implant, converts received sound into a mechanical force that is applied to the ossicular chain or directly to the cochlea via an actuator implanted in or adjacent to the middle ear cavity. Conversely, cochlear implants can have utilitarian value with respect to recipients where all of the inner hair inside the cochlea has been damaged or otherwise destroyed. Electrical impulses are provided to electrodes located inside the cochlea, which stimulate nerves of the recipient so as to evoke a hearing percept.

SUMMARY

In accordance with one aspect, there is an implantable apparatus, comprising an implantable transducer fixation mechanism, the fixation mechanism being configured to receive an implantable transducer, wherein the fixation mechanism is configured to be fixed to a wall of the middle ear cavity of the recipient, and the fixation mechanism is configured to locate the transducer at least partially outside the middle ear cavity.

In accordance with another aspect there is a method, comprising obtaining access to a recipient; and fixing a transducer in a recipient such that the transducer is at least partially located outside a middle ear cavity by securing the transducer to structure of the recipient in the middle ear cavity.

In accordance with another aspect, there is an implantable apparatus, comprising an implantable transducer fixation mechanism, the fixation mechanism being configured to receive an implantable transducer, and a middle ear transducer, wherein the middle ear transducer is incompatible with complete placement in a middle ear, wherein the implantable transducer fixation mechanism is a growing child compatible fixation mechanism.

In accordance with another aspect, there is a method, comprising, activating a middle ear transducer implanted in a recipient, and transducing first energy indicative of sound via the middle ear transducer for a first time after an implantation procedure of the transducer is fully completed, wherein the middle ear transducer is located at least partially outside the middle ear cavity, and the middle ear transducer is only fixed to structure inside the middle ear cavity.

BRIEF DESCRIPTION OF THE DRAWINGS

Some embodiments are described below with reference to the attached drawings, in which:

FIGS. 2A and 2B are schematic diagrams illustrating exemplary middle ear implants according to some exemplary embodiments;

FIG. 3 depicts an exemplary embodiment of an implanted tube microphone utilized in conjunction with a cochlear implant;

FIGS. 4A and 4B illustrate some exemplary embodiments of the exemplary tube microphones;

FIGS. 5-8 illustrate exemplary embodiments of an implantable apparatus;

FIGS. 25A to 27 present some alternate exemplary embodiments;

DETAILED DESCRIPTION

Aspects of the present invention are generally directed to an implantable component of a middle ear hearing prosthesis. A middle ear transducer is operationally coupled to the receiver-stimulator, and a transducer fixation mechanism is connected to (in some embodiments, is an integral part of) the transducer, and extends from the transducer into the middle ear cavity. While some of the embodiments detailed herein are directed towards hearing prostheses in general and middle ear implants (direct acoustic cochlear stimulator, as such is sometimes referred to) in particular, other embodiments include a transducer fixation mechanism usable as detailed herein and variations thereof can be implemented. Moreover, while the teachings detailed herein are sometimes directed towards a transducer in the form of a microphone, any such disclosure corresponds to a disclosure in an alternate embodiment of a transducer and form of an actuator (and vice versa). Also, while the embodiments detailed herein are directed towards an embodiment where the prosthesis is a middle ear hearing prosthesis, in other embodiments, the teachings detailed herein, such as those associated with the embodiments where the transducer is a microphone, can be practiced with other types of hearing prostheses, such as a cochlear implant, which could be used to establish a totally implantable hearing prostheses.

Figure 1:
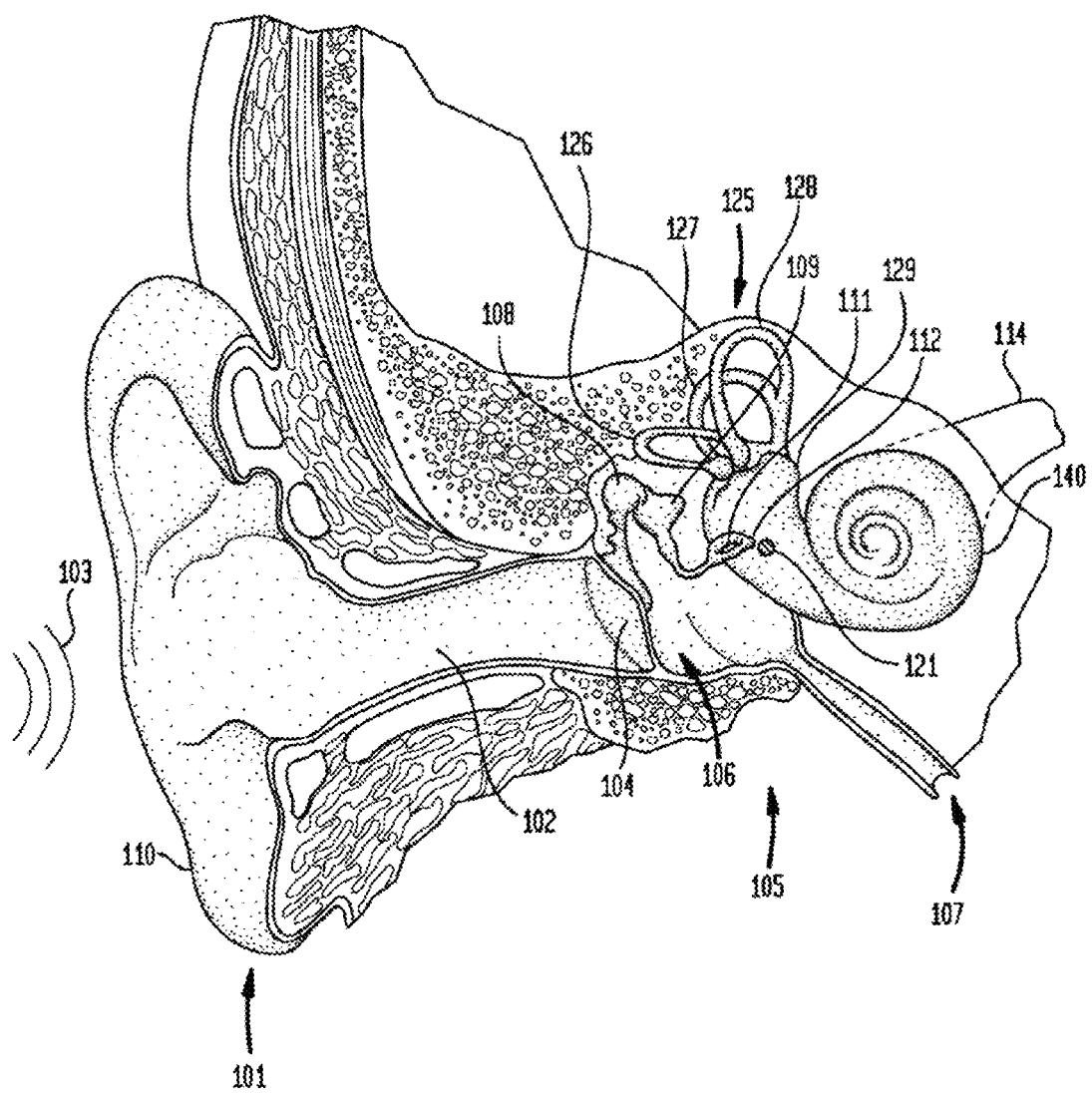
FIG. 1 is a perspective view of an exemplary bone conduction device in which at least some embodiments can be implemented.

FIG. 1 is a perspective view of a human skull showing the anatomy of the human ear. As shown in FIG. 1, the human ear comprises an outer ear 101, a middle ear 105, and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121. This vibration is coupled through three bones of middle ear 105, collectively referred to as the ossicles 106 and comprising the malleus 108, the incus 109, and the stapes 111. Bones 108, 109, and 111 of middle ear 105 serve to filter and amplify sound wave 103, causing oval window 112 to articulate, or vibrate in response to the vibration of tympanic membrane 104. This vibration sets up waves of fluid motion of the perilymph within cochlea 140. Such fluid motion, in turn, activates hair cells (not shown) inside cochlea 140. Activation of the hair cells causes nerve impulses to be generated and transferred through the spiral ganglion cells (not shown) and auditory nerve 114 to the brain (also not shown) where they cause a hearing percept.

As shown in FIG. 1, semicircular canals 125 are three half-circular, interconnected tubes located adjacent cochlea 140. Vestibule 129 provides fluid communication between semicircular canals 125 and cochlea 140. The three canals are the horizontal semicircular canal 126, the posterior semicircular canal 127, and the superior semicircular canal 128. The canals 126, 127, and 128 are aligned approximately orthogonally to one another. Specifically, horizontal canal 126 is aligned roughly horizontally in the head, while the superior 128 and posterior canals 127 are aligned roughly at a 45 degree angle to a vertical through the center of the individual's head.

Each canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

Figure 2A:
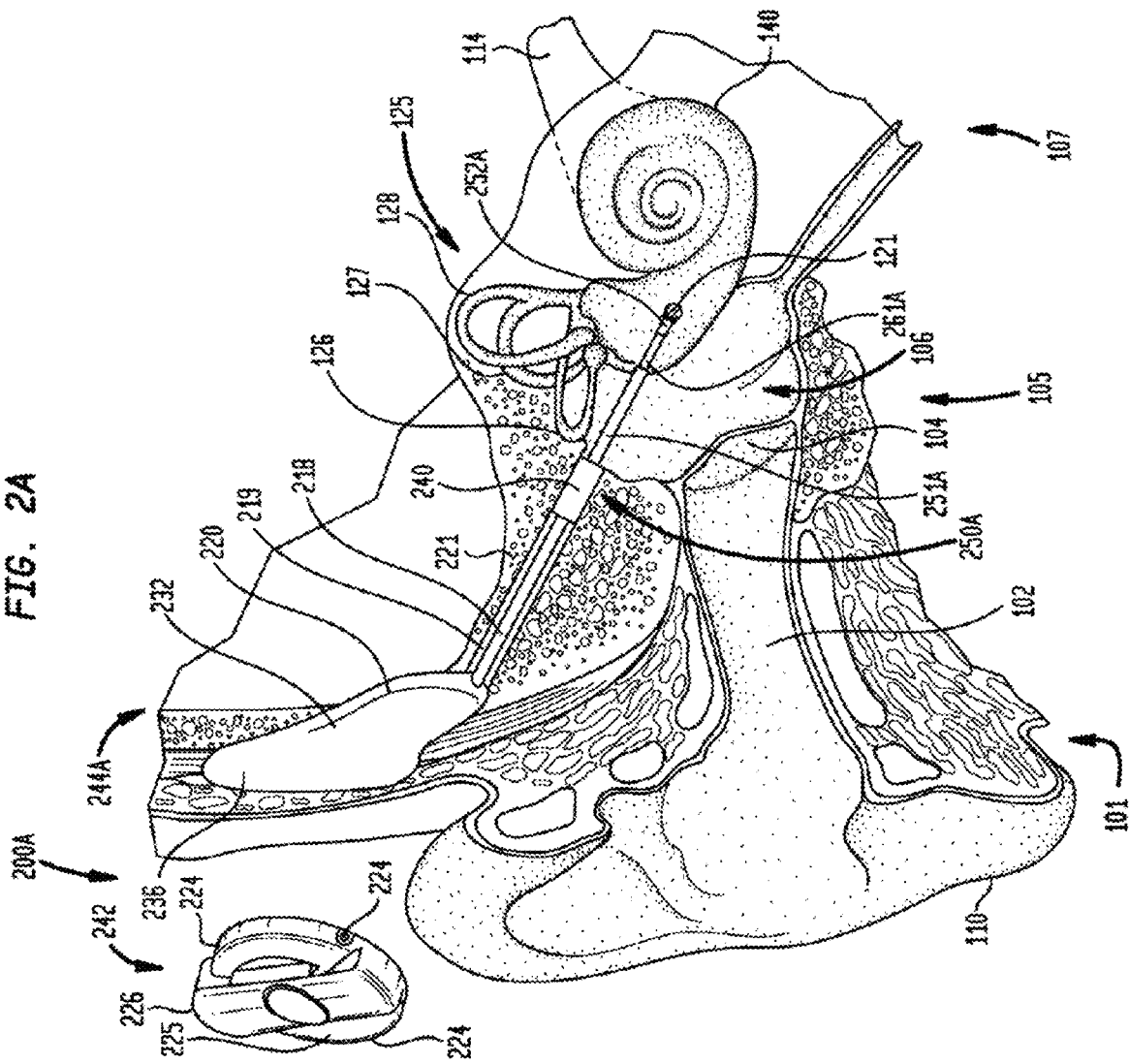

FIG. 2A is a perspective view of an exemplary direct acoustic cochlear stimulator 200A in accordance with embodiments of the present invention. (Sometimes herein, this is referred to as a middle ear implant.) Direct acoustic cochlear stimulator 200A comprises an external component 242 that is directly or indirectly attached to the body of the recipient, and an internal component 244A that is temporarily or permanently implanted in the recipient. External component 242 typically comprises two or more sound input elements, such as microphones 224, for detecting sound, a sound processing unit 226, a power source (not shown), and an external transmitter unit 225. External transmitter unit 225 comprises an external coil (not shown). Sound processing unit 226 processes the output of microphones 224 and generates encoded data signals which are provided to external transmitter unit 225. For ease of illustration, sound processing unit 226 is shown detached from the recipient. Internal component 244A comprises an internal receiver unit 232, a stimulator unit 220, and a stimulation arrangement 250A in electrical communication with stimulator unit 220 via cable 218 extending through artificial passageway 219 in mastoid bone 221. Internal receiver unit 232 and stimulator unit 220 are hermetically sealed within a biocompatible housing, and are sometimes collectively referred to as a stimulator/receiver unit.

Internal receiver unit 232 comprises an internal coil (not shown), and optionally, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated platinum or gold wire. The electrical insulation of the internal coil is provided by a flexible silicone molding (not shown). In use, implantable receiver unit 232 is positioned in a recess of the temporal bone adjacent auricle 110.

In the illustrative embodiment of FIG. 2A, ossicles 106 have been explanted. However, it should be appreciated that stimulation arrangement 250A may be implanted without disturbing ossicles 106.

Stimulation arrangement 250A comprises an actuator 240, a stapes prosthesis 252A and a coupling element 251A which includes an artificial incus 261B. Actuator 240 is osseointegrated to mastoid bone 221, or more particularly, to the interior of artificial passageway 219 formed in mastoid bone 221.

In this embodiment, stimulation arrangement 250A is implanted and/or configured such that a portion of stapes prosthesis 252A abuts an opening in one of the semicircular canals 125. For example, in the illustrative embodiment, stapes prosthesis 252A abuts an opening in horizontal semicircular canal 126. In alternative embodiments, stimulation arrangement 250A is implanted such that stapes prosthesis 252A abuts an opening in posterior semicircular canal 127 or superior semicircular canal 128.

As noted above, a sound signal is received by microphone(s) 224, processed by sound processing unit 226, and transmitted as encoded data signals to internal receiver 232. Based on these received signals, stimulator unit 220 generates drive signals which cause actuation of actuator 240. The mechanical motion of actuator 240 is transferred to stapes prosthesis 252A such that a wave of fluid motion is generated in horizontal semicircular canal 126. Because vestibule 129 provides fluid communication between the semicircular canals 125 and the median canal, the wave of fluid motion continues into the median canal, thereby activating the hair cells of the organ of Corti. Activation of the hair cells causes appropriate nerve impulses to be generated and transferred through the spiral ganglion cells (not shown) and auditory nerve 114 to cause a hearing percept in the brain.

FIG. 2B depicts an exemplary embodiment of a middle ear implant 200B having a stimulation arrangement 250B comprising actuator 240 and a coupling element 251B.

Coupling element 251B includes a stapes prosthesis 252B and an artificial incus 261B which couples the actuator to the stapes prosthesis. In this embodiment, stapes prosthesis 252C abuts stapes 111.

FIG. 3 is perspective view of a totally implantable cochlear implant, referred to as cochlear implant 100, implanted in a recipient. As shown, cochlear implant 100 comprises one or more components which are temporarily or permanently implanted in the recipient. Cochlear implant 100 is shown in FIG. 3 with an external device 142 which, as described below, is configured to provide power to the cochlear implant.

In the illustrative arrangement of FIG. 3, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. As would be appreciated, various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 3 is merely illustrative, and other external devices may be used with embodiments of the present invention.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In embodiments of the present invention, internal energy transfer assembly 132 and main implantable component 120 are hermetically sealed within a biocompatible housing. In embodiments of the present invention, main implantable component 120 includes a sound processing unit (not shown) to convert the sound signals received by the implantable microphone in internal energy transfer assembly 132 to data signals. Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. As noted, a stimulator unit generates stimulation signals which are applied by electrodes 148 to cochlea 140, thereby stimulating auditory nerve 114.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in main implantable component 120, or disposed in a separate implanted location.

Stimulator 132 receives a signal generated by an implanted sound sensor 150, in this embodiment, via a cable 162. Sound sensor 150 is implanted in a cavity formed in mastoid bone 119 so as to extend, in this embodiment, into the middle ear cavity. Sound sensor 150 is configured to detect sound received in a recipient's ear through the use of vibrations or pressure variations that occur in or along the natural path that is followed by acoustic waves in the ear. More specifically, sound sensor 150 senses vibration of a structure of the recipient's ear or vibration of fluid within one of the recipient's body cavities, such as recipient's middle ear cavity, inner ear canals, cochlear ducts, etc. The vibration of the recipient's ear structure, or the vibration of the fluid within a body cavity is a result of the receipt of acoustic waves that travel from the recipient's outer ear to the middle and inner ear. That is, the received acoustic waves result in the vibration of the middle or inner ear structures, or travel through the middle ear cavity, creating vibration of the fluid within the cavities. In the embodiment illustrated in FIG. 3, the sound sensor detects sound based on vibration of the recipient's middle ear bones, and more specifically, based on vibration of incus 109.

An embodiment of implantable sound sensor 150 is described next below with reference to FIGS. 4A and 4B, referred to herein as implantable sound sensor 250. Implantable sound sensor 250 comprises a housing 258 having, in this embodiment, a substantially tubular shape. The tubular shape may have a cylindrical or elliptical cross-sectional shape. Other shapes, such as prismatic with square, rectangular, or other polygonal cross-sectional shapes may also be used in alternative embodiments. However, a cylindrical shape may be advantageous for purposes of implantation and manufacture.

Figure 4A:
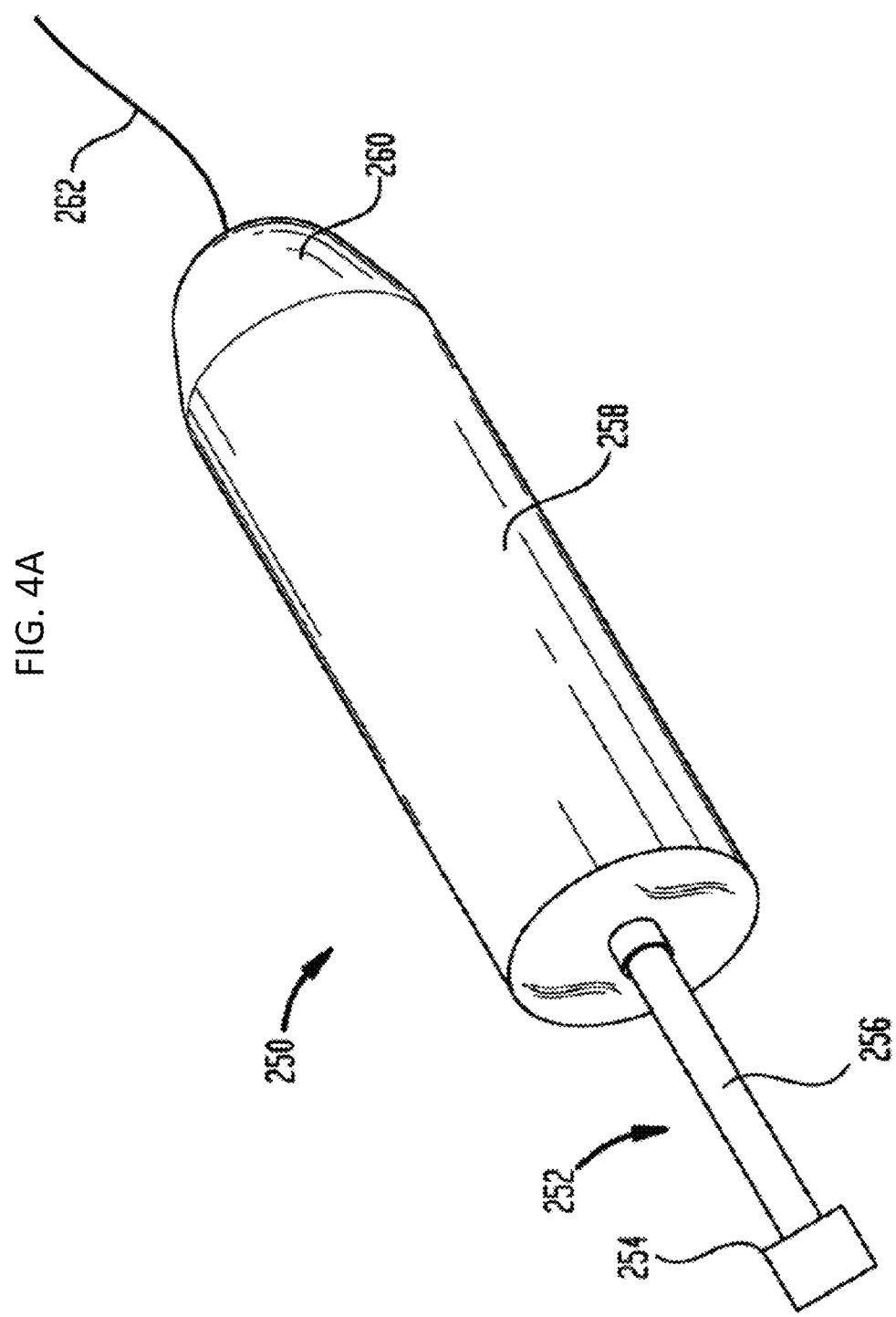

In the embodiments of FIGS. 4A and 4B, housing 258 is closed at one end 246 by a membrane 248. Membrane 248 is connected to housing 258 as to hermetically seal the one end 246. Membrane 248 may be connected to housing 258 through one of many known techniques, such as laser welding or manufacturing (milling, turning) housing 258 and membrane 248 out of one piece.

Housing 258 is closed at the opposing end 264, that is, the end remote from membrane 248, by a closure 260. Closure 260 also provides a hermetical seal. Hence, housing 258, membrane 248 and closure 260 form a biocompatible hermetically-sealed enclosure that is substantially impenetrable to air and body fluids.

In embodiments of the present invention, membrane 248 is substantially flexible and is configured to vibrate. The thickness of membrane 248 is selected depending on, for example, the material of which it is made and the body location in which sound sensor 250 will be implanted. Additionally, membrane 248 and housing 258 may be each made from the same or different titanium or a titanium alloy. However, it would be appreciated that other biocompatible materials may also be used. For example, in one alternative embodiment, closure 260 may be manufactured of a biocompatible ceramic material.

A coupling mechanism 252 is secured to the exterior surface of membrane 248. In the embodiment illustrated in FIGS. 4A and 4B, coupling mechanism 252 comprises an elongate rod 256 and a bracket 254 disposed on the distal end of the rod. Bracket 254 may have a variety of configurations depending on which structure of the natural ear the device is to be secured. This is described in further detail below.

A vibrational sensor 272, such as a microphone, is disposed inside housing 258. In certain such embodiments, the vibrational sensor is a pressure sensitive transducer configured to generate an electrical signal in response to detected pressure waves. Microphone 272 may be arranged such that the microphone's sensing element is located proximal to membrane 248 with a defined gas layer 275 positioned between the microphone's sensing element and the membrane. The microphone's sensing element is typically a diaphragm.

The housing 258 is a cylindrical component, as can be seen. The cylindrical component has an outer diameter of more than 3 mm and a length of more than 3 mm. In an exemplary embodiment, the outer diameter is equal to or more than 3.5, 4, 4.5, 5, 5.5, 6, 6.5, 7, 7.5, or 8 mm, or any value or range of values therebetween in 0.05 mm increments. In an exemplary embodiment, the outer length is equal to or more than 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16 mm, or any value or range of values therebetween in 0.05 mm increments. In an exemplary embodiment, the microphone 250 has any one or more or all of the features of the transducer disclosed in U.S. patent application Ser. No. 12/997,788, entitled Implantable Sound Sensor for Hearing Prostheses, to Koen Erik Van den Heuvel.

In the above embodiments, as coupling mechanism 252 vibrates membrane 248, the excitation of the membrane is transmitted to the inside of housing 258, where it is sensed by microphone 272. Microphone 272 may be an electret microphone, such as from Sonion (Denmark) or Knowles (USA). Other types of microphones may be used as well, such as: magnetic, dynamic, piezo-electric, optical, or electro-mechanical.

In an alternative embodiment, vibrational sensor 272 is an accelerometer suitable for sensing vibrations of membrane 248. In one particular embodiment, vibrational sensor 272 is a micro-electromechanical system accelerometer.

Vibrational sensor 272 is connected to housing 258 by means of a fluid suspension 276, which is preferably made of, or that comprises, silicone. It should be appreciated that in alternative embodiments, other mechanisms may be implemented to isolate vibrational sensor 272 from the motion of sound sensor 250.

Implantable sound sensor 250 further comprises a transmitter for transmitting the signal generated by vibrational sensor 272, either raw or processed, to an element outside of sound sensor 250, such as to an implantable stimulation device or other component of an implantable hearing prosthesis.

The transmitter may comprise an electronic circuit 270 mounted inside housing 258 that is coupled to microphone 272 by wires 262. Electronic circuit 270 may be configured to process the signal generated by the microphone 272 for transmission to an implantable stimulation device.

Electronic circuit 270 may be configured to convert alternating electrical current (AC) to direct electrical current (DC) and to deliver electrical power to the microphone 272. In the embodiment of FIGS. 2A and 2B, electrical power is provided from a source outside of sensor 250 through wires 262 (through AC current). In alternative embodiments, a battery can be provided inside housing 258.

At least one feedthrough 266 is preferably provided for passing electrical wires 262 to through housing 258. Feedthrough 266 is preferably provided through closure 260. In certain embodiments, feedthrough 266 is formed in closure 260; in other words, they are unitary.

Electrical wires 262 may be configured to pass electrical power to implantable device 250. Wires 262 may be configured to transmit the processed microphone signal to the exterior of sound sensor 250. In the latter case, electronic circuit 270 may be configured to modulate the signal on the power wires.

In an alternative embodiment, the transmission is wireless. In such embodiments the implantable device 250 may be provided with an electromagnetic antenna (not shown).

The enclosure, formed by housing 258, membrane 248, and closure 260, is, in certain embodiments, filled with an inert gas, such as nitrogen or argon.

Rod 256 is an elongate member suitable for coupling membrane 248 to a vibrating structure of the ear. Alternatively, the sound sensor 250 may comprise one or more brackets 254 for additionally connecting membrane 248 to a structure of the middle or inner ear. In certain embodiments, rod 256 or bracket 254 may be coupled to the tympanic membrane, and bracket 254 may be a bracket similar to those used for tympanoplasty. That is, bracket 254 may comprise a disc for coupling to the tympanic membrane. Additionally, in other embodiments, rod 256 or bracket 254 may be coupled to the malleus, the incus, or the stapes, and bracket 254 may comprise, for example, a bracket such as those used for stapedioplasty. In such embodiments, bracket 254 comprises a clip for coupling to one of those structures. In still other embodiments, rod 256 or bracket 254 may be coupled to the elliptical window, round window, the horizontal canal, the posterior canal or the superior canal.

Figure 5:
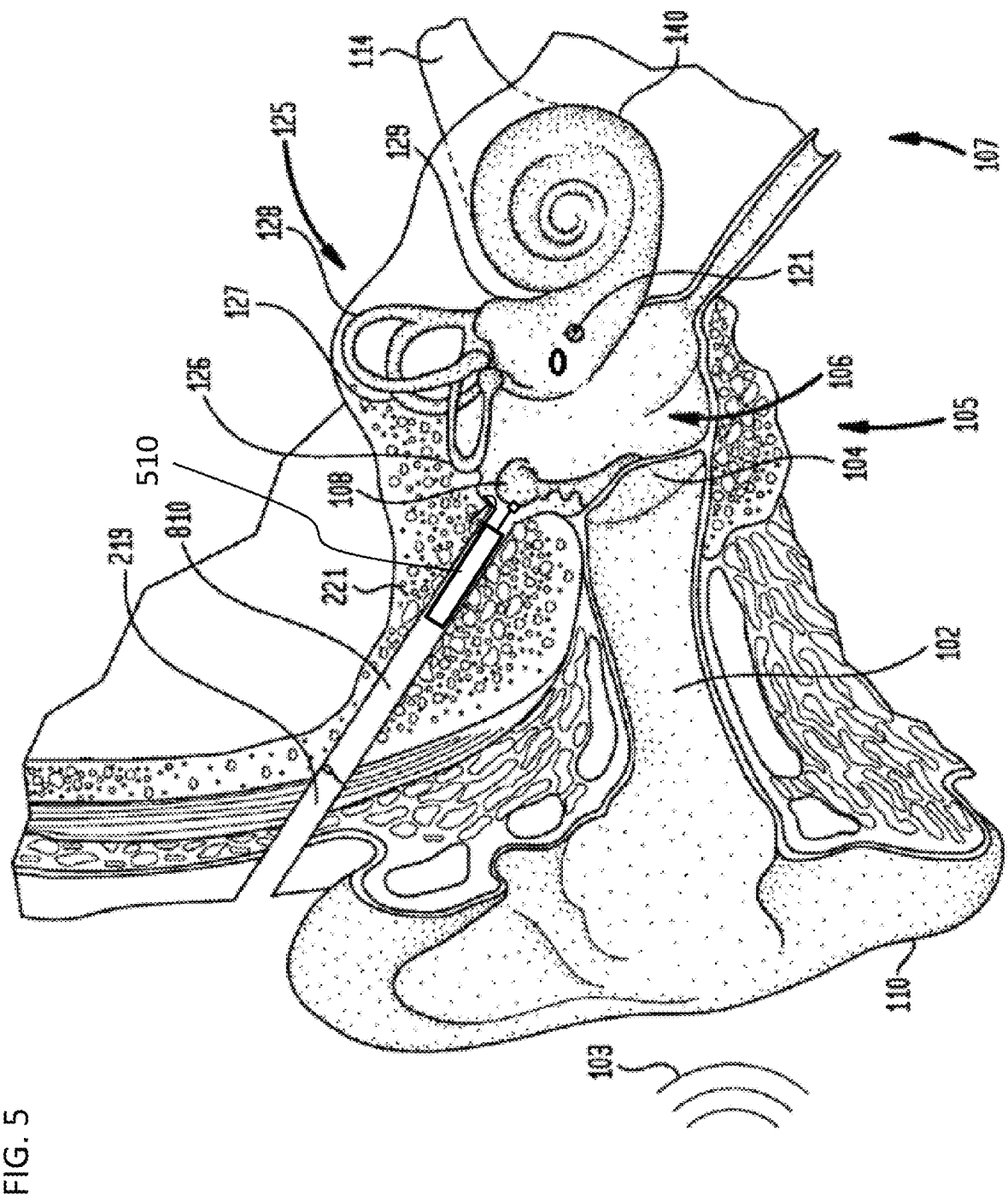

FIG. 5 is a perspective view of an exemplary embodiment where a cavity borer or the like has drilled from the outer surface of the mastoid bone 221 straight to the middle ear cavity 106 to establish artificial passageway 219, in which the microphone and/or the middle ear actuator detailed above can be inserted. That said, in alternate embodiments, the passageway 219 may not be straight and the passageway 219 might not be drilled from the outer surface of the mastoid bone 221 but instead from the middle ear cavity 106, and in some embodiments, the passageway 219 might not extend completely from the middle ear cavity to the external surface. Any arrangement of passageway that can have utilitarian value can be utilized in some embodiments.

Figure 6:
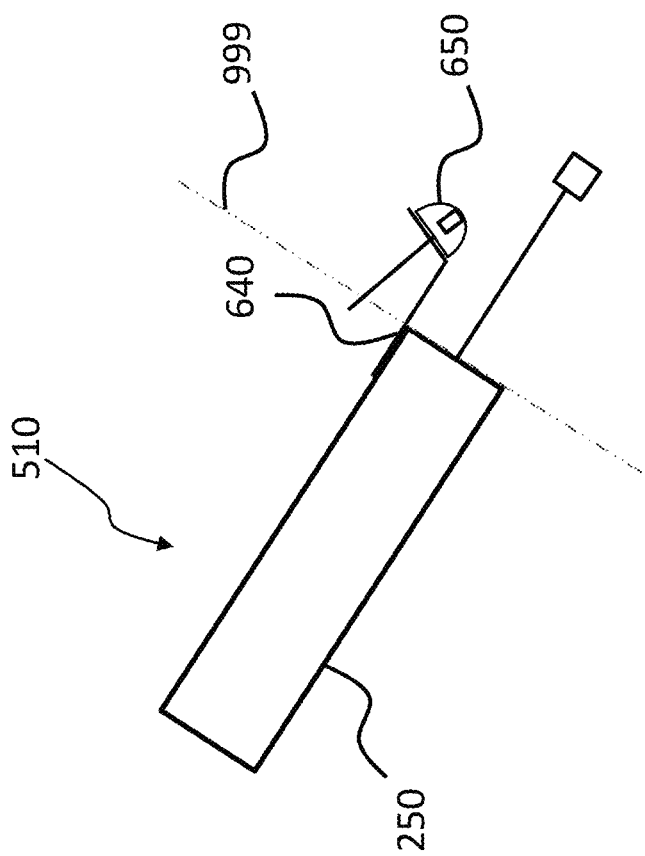

FIG. 5 is also an exemplary embodiment of an exemplary implantable apparatus 510, comprising, now with reference to FIG. 6, a tube microphone 250 and an implantable transducer fixation mechanism 640, the fixation mechanism 640 being configured to receive the implantable transducer 250. As can be seen, a bone screw 650 is also included with the fixation mechanism 640, which bone screw is used to fix the fixation mechanism to the wall of the middle ear cavity of the recipient, as seen in FIG. 5. Thus, the fixation mechanism 640 is configured to be fixed to a wall of the middle ear cavity of the recipient. In the embodiment of FIGS. 5 and 6, the fixation mechanism 640 is configured to locate the transducer 250 at least partially outside the middle ear cavity. It is noted that while the embodiments herein reference a tube microphone as the exemplary microphone, in other embodiments, other types of microphones can be used. Also, other types of transducer sensors other than microphones can be used. Any transducer sensor that can be used in a utilitarian manner with the teachings detailed herein can be used in some embodiments.

It is briefly noted that while the embodiments of FIGS. 5 and 6 focus on the tube mic embodiment of FIGS. 4A and 4B, in alternate embodiments, as will be described in greater detail below, the aforementioned implantable transducer can be the middle ear actuator of the embodiments of FIGS. 2A and 2B. Any type of transducer that can be utilized with the teachings detailed herein can be utilized in at least some exemplary embodiments.

As seen from FIG. 5 in an exemplary embodiment, the fixation mechanism 640 is configured to locate the transducer 50 at least partly outside the middle ear cavity 106, and completely outside the outer ear passageway 102. That is, no part of the transducer is located in the outer ear passageway 102, as might be the case in at least some exemplary embodiments where the transducer extends through the tympanic membrane 104.

Figure 6A:
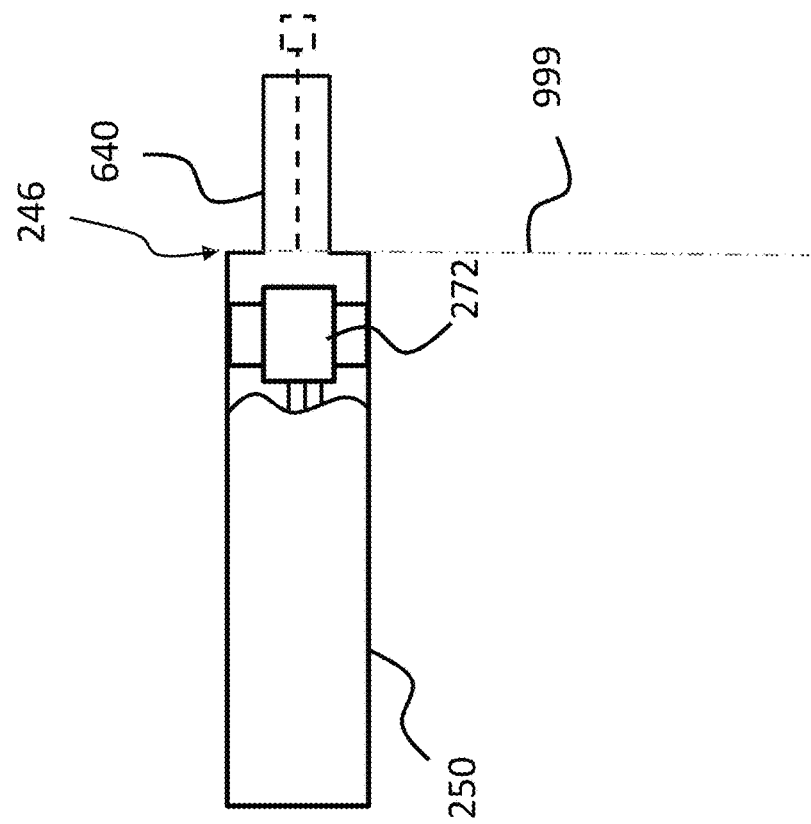

In the embodiment of FIG. 6, the fixation mechanism 640 is an integral part of the transducer. By way of example only and not by way of limitation, the fixation mechanism 640 can include an elongate plate of titanium that is welded to the transducer housing 258 on the outside of the wall of the housing and extends forward away from the membrane 248. That said, in an alternate embodiment, the fixation mechanism 640, or at least a portion thereof, can potentially be a portion that is monolithic with at least a portion of the wall of the housing 258. In this regard, FIG. 6A depicts an exemplary embodiment of a tube mic 250 where a portion of the wall of the housing 258 at the front end 246 of the housing 258 has been removed so as to depict the interior of the housing, and diaphragm 248 has been removed as well, and the coupling mechanism 252 is depicted in dashed lines for reference. As can be seen, the fixation mechanism 640 extends in a seamless manner from the wall of the housing 250. In this embodiment, the fixation mechanism 640 is a monolithic part of the housing wall.

By "integral," it is meant at least that in order to remove the transducer from the recipient, at least a portion of the fixation mechanism will also have to be removed with the transducer (e.g., if not the entire portion, the fixation mechanism will have to be cut in half or the like). This is as opposed to a fixation mechanism that is configured to be removably attached to the transducer.

Figure 8:
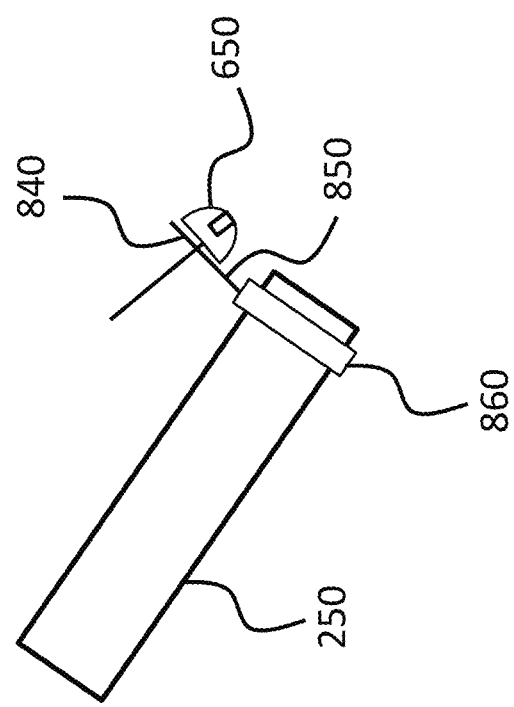

FIGS. 7 and 8 depict an alternate embodiment of an implantable apparatus 710, which includes a fixation mechanism 840, where the fixation mechanism 840 includes a plate 850 extending from a band 860 that extends about the transducer 250. The plate 850 has a hole therethrough so as to receive the bone screw 650, or, more accurately, so that the bone screw 650 can be extended through the hole and thus the fixation mechanism 840 can be fixed to the wall of the middle ear cavity. In an exemplary embodiment, the band 860 is welded to the housing of the transducer 250. That said, in an alternate embodiment, the band 860 is interference fitted about the housing 250. Still further, in an exemplary embodiment, the band 860 is slip fit about the housing 250, and other components, such as screws or detents or the like are used to keep the transducer 250 from moving in the axial direction and/or the radial direction. Any device, system, and/or method of connecting the transducer 250 to the fixation mechanism can be utilized in at least some exemplary embodiments.

It is noted that the embodiments of FIGS. 7 and 8 correspond to an alternate embodiment where there is no coupling mechanism 242 secured to the exterior surface of the membrane 248. Instead, the pressure changes within the middle ear cavity that results movement of the tympanic membrane are sufficient to move the membrane 248 of the microphone 250. Any embodiment of transducer that can be utilized to practice the teachings detailed herein can be utilized in at least some exemplary embodiments.

In some exemplary embodiments, the fixation mechanism includes a transducer cradle or the like that is configured to releasable receive the transducer, and the fixation mechanism is configured such that the cradle or the like is at least partially located outside the middle ear cavity when the fixation mechanism is secured to the wall. An exemplary embodiment of such is disclosed in US patent application publication no. 2013/0225912 entitled Combined Functional Component and Implantable Actuator Positioning Mechanism and US patent application publication no. 2013/0165737 entitled Implantation of a Hearing Prosthesis, respectively to Roger Leigh and Koen Van den Heuvel, respectively.

Figure 8A:
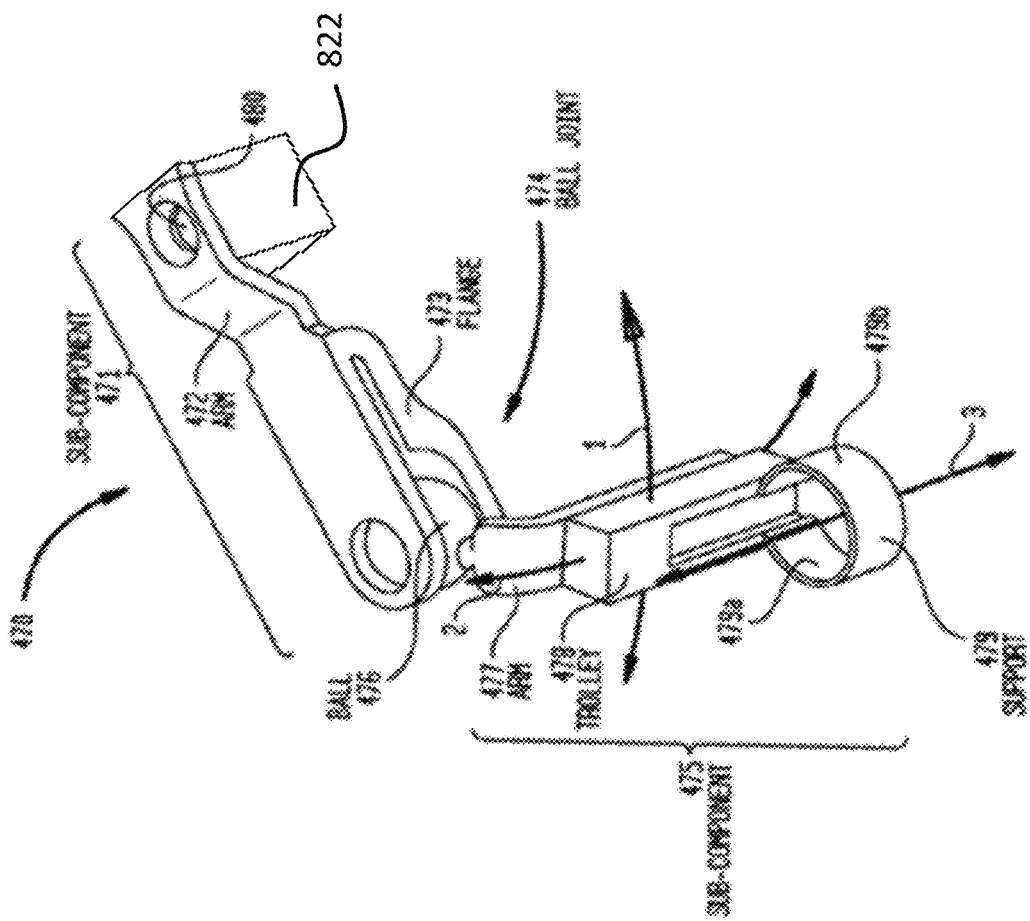
FIG. 8A illustrates an exemplary transducer positioning mechanism according to some exemplary embodiments.

In some embodiments, irrespective of whether the transducer is releasable or not from the fixation mechanism, the fixation mechanism is configured to enable the transducer to move relative to a component of the fixation mechanism fixed to the wall, thereby enabling the transducer to be adjustably positioned at a location at least partially outside the middle ear cavity when the fixation mechanism is fixed to the wall. In this regard, FIG. 8A depicts a transducer fixation mechanism that is also a transducer positioning mechanism 470 as comprising two sub-components: extension arm 471 and extension arm 475. Sub-component 471 includes arm 472 that is configured to be attached to the middle ear cavity, where spacer 822 is present to lift the arm away from the surface of the middle ear cavity to provide room for the flange 473 (discussed below). In this regard, it is noted that the transducer support mechanism may be made partially or totally out of titanium. Sub-component 471 also includes flange 473 which forms a female portion of ball joint 474. In this regard, sub-component 475 includes the male portion of the ball joint 474, in the form of a ball 476, as may be seen. Ball joint 474 permits the ball 476 of sub-component 475 to move within the female portion, thereby permitting sub-component 475 to articulate relative to sub-component 471, and thus permitting transducer 250 to likewise articulate relative to the middle ear cavity.

It is briefly noted that any disclosure associated with the embodiment of FIG. 8A/any disclosure associated with the transducer positioning mechanism can be utilized in the transducer fixation mechanism that does not include the positioning features, and vice versa. Indeed, this is nothing more than an embodiment that is concomitant with the fact that any single feature of any given embodiment detailed herein can be combined with any other feature of any other embodiment detailed herein providing that the art enable such.

Ball joint 474 enables the transducer 250 to be positioned at an adjustably fixed location relative to the passageway 219 and/or the components of the middle ear and/or the components of the cochlea. In an exemplary embodiment, the ball joint 474 permits the location of the transducer 250 to be adjustable relative to the middle ear cavity in two degrees of freedom, represented by arrows 1 and 2 (first and second degrees of freedom, respectively), in FIG. 8A, although in some embodiments the joint may permit the location of the transducer to be adjustable only one degree of freedom or in more than two degrees of freedom.

While transducer positioning mechanism 470 is depicted with a ball joint 474, other types of joints may be utilized. By way of example, the joint may comprise a malleable portion of a structural component of the transducer positioning mechanism 470 that permits the transducer 250 to be positioned as just detailed or variations thereof. In an exemplary embodiment, the joint is an elastically deformable portion or plastically deformable portion or is a combination of elastically deformable and plastically deformable portions so as to enable the adjustment of the location of the received transducer relative to the implant body in the at least one degree of freedom.

As noted above, transducer positioning mechanism 470 further includes sub-component 475. Sub-component 475 comprises ball 476 of ball joint 474, arm 477, trolley 478 and transducer support 479. Transducer support 479 is depicted as being in the form of a collar, and receives and otherwise holds transducer 250 therein, and thus holds the transducer 250 to the transducer positioning mechanism 470.

The collar has an exterior surface 479a and an interior surface 479b, configured to receive transducer 250. The interior diameter of the collar, formed by interior surface 479b is approximately the same as the outer diameter of the cylindrical body of the transducer 250. The outer diameter of the collar, formed by exterior surface 479a, is sized such that the collar will fit into the artificial passageway 219. The length of the collar is shorter than the cylindrical body of the transducer 250, but in other embodiments, it may be the same length or about the same length or longer. As noted, transducer support 479 and transducer 250 are configured to enable the transducer 250 to be removably secured to the transducer support 479, and thus the transducer positioning mechanism 470. This removable securement may be, in some embodiments, sufficient to prevent transducer 250 from substantially moving from the retained location in the transducer support 479, and the transducer positioning mechanism 470 is configured to prevent the transducer support 479 from substantially moving within the artificial passageway 219 during operation of the transducer 250. For example, the removable securement may be achieved via an interlock between the transducer 250 and the collar that provides retention sufficient to withstand reaction forces resulting from operation of transducer 250.

In an exemplary embodiment, the interlock is provided by an interference fit between inner surface 479a of the collar of transducer support 479 and an outer surface of transducer 250. In an alternate embodiment, the interlock is implemented as threads of inner surface 479a that interface with corresponding threads on the outer surface of transducer 250. In another embodiment, O-rings or the like may be used to snugly wrap around transducer 250 and snugly fit inside the collar of transducer support 479. Grooves on the transducer 250 and/or on the collar may be included to receive the O-ring. In other embodiments, compression of the O-ring between the transducer 250 and the collar provides sufficient friction to retain the components in the transducer support 479. In another embodiment, transducer support 479 or transducer 250 includes a biased extension that is adjusted against the bias to insert the transducer into the support. The extension may engage a detent on the opposing surface to interlock the transducer and the support. Other embodiments include protrusions and corresponding channels on opposing surfaces of the transducer and support. An exemplary embodiment includes a spring-loaded detent that interfaces with a detent receiver of the opposing surface to hold the transducer in the support or that extends behind the transducer once the transducer has been positioned beyond the detent. An alternate embodiment may utilize O-rings to interlock the transducer in the support. Adhesive may be used to interlock the transducer in the support. Any device, system, or method that will interlock transducer in the support that will permit embodiments detailed herein and/or variations thereof to be practiced may be utilized in some embodiments.

The trolley 478, which is rigidly connected to transducer support 479, is configured to move linearly in the direction of arrow 3 parallel to the longitudinal direction of extension of arm 477. In this exemplary embodiment, arm 477 includes tracks with which trolley 478 interfaces to retain trolley 478 to arm 477. These tracks also establish trolley 478 and arm 477 as a telescopic component configured to enable the adjustment of the location of transducer support 479, and thus transducer 250 when received therein, relative to the housing 446 (thus the implant body), in at least one degree of freedom (i.e., the degree of freedom represented by arrow 3). It is noted that other embodiments may permit adjustment in at least two or at least three degrees of freedom. Thus, when the trolley component is combined with the aforementioned joint 474, the transducer positioning system enables the location of the transducer 250 to be adjustable relative to the implant body in at least two or at least three degrees of freedom.

Movement of the trolley 478 along arm 477 may be accomplished via a jack screw mechanism where the jack screw is turned via a screw driver or a hex-head wrench. Movement of the trolley 478 may also or alternatively be achieved via application of a force thereto that overcomes friction between the trolley 478 and the arm 477. Any device, system, or method that permits trolley 478 to move relative to arm 477 may be used in some embodiments detailed herein and variations thereof.

Referring to FIG. 8A, it can be seen that arm 472 of transducer positioning mechanism 470 includes screw hole 480. Screw hole 480 is configured to receive a bone screw. While screw hole 480 is depicted as being located on (in) arm 472, in other embodiments, screw holes may be located elsewhere on the middle ear implant internal component (and bone screws may be received therein).

In general, as can be seen from FIG. 5, some exemplary embodiments are such that the fixation mechanism is configured to extend from an artificial passageway 219 that extends through a temporal bone (mastoid bone) into the middle ear cavity. Conversely, some exemplary embodiments of the fixation mechanism are such that the entire fixation mechanism is away from/is not in the artificial passageway that extends through a temporal bone into the middle ear cavity, such as is seen in FIG. 7.

In at least some embodiments, the artificial passageway 219 has a circular cross-section that is between about 1 to 10 mm in diameter, and, in some embodiments, more than X but less than Y, where X is any applicable value of 1, 2, 3, 4, 5, 6, 7, 8, 9, 10, 11, 12, 13, 14, or 15 mm and Y is any applicable value of 2, 3, 4, 5, 6, 7, 8, 9, 10, 11, 12, 13, 14, 15, 16, 17, 18 mm. In an exemplary embodiment, the diameter of the passageway is about 0.5, 0.75, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 13, 14, 15, 16, 17, or 18 mm, or any value or range of values therebetween in about 0.01 mm increments (e.g., 7.04 mm, 9.99 mm, about 3.34 mm to about 14.41 mm, etc.). It is noted that the aforementioned values can be the diameter at a location where the fixation mechanism is located. By way of example, any plane that is normal to the longitudinal axis of the passageway that bisects a portion of the fixation mechanism is a location where the fixation mechanism is located in the passageway.

In view of the above, it can be seen that in some embodiments, the implantable apparatus includes a transducer that is in the form of a tube microphone that includes a vibration input portion, wherein the fixation mechanism includes a fixation arm that extends away from the vibration input portion and the vibration input portion faces the fixation arm, and the fixation arm is configured to be secured to the recipient in the middle ear cavity of the recipient. An exemplary embodiment of this is seen in FIGS. 6 and 6A, where at least a portion of the component of fixation mechanism 640 that projects past the end of the housing of fixation mechanism 640 (e.g., the portion extending past reference line 999 in the figures) is a fixation arm that extends away from the vibration input portion (e.g., the membrane of the tube mic) where that vibration input portion (again, the membrane), faces the fixation arm. (It is noted that the term "faces" does not require direct alignment, as can be seen from these examples. By way of example, an archer on an archery range with an array of targets faces a number of targets beyond one that he or she is directly aligned with, but would not face targets located, for example, to the absolute left or the absolute right or behind him or her.)

Figure 9:
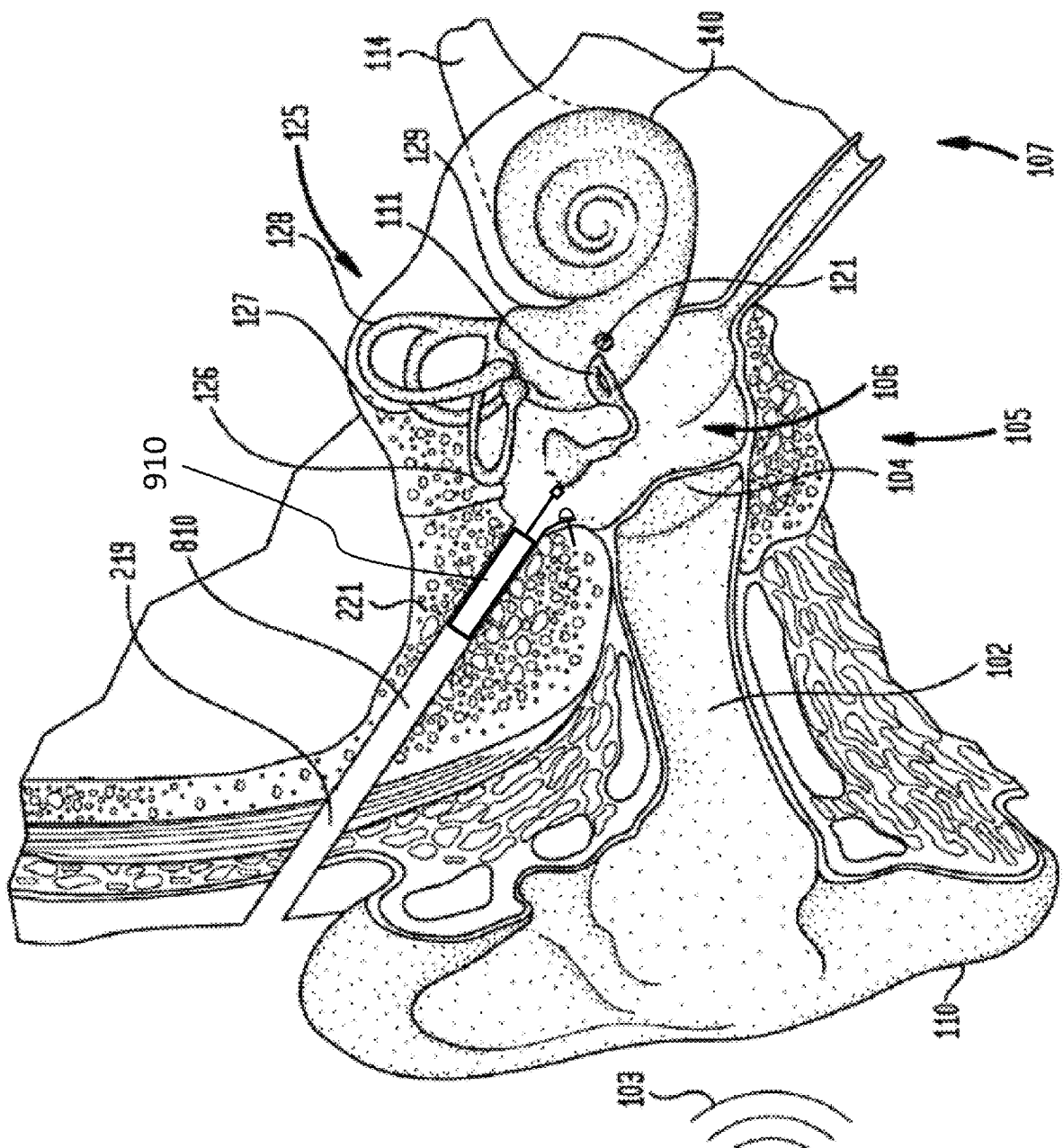
FIGS. 9 and 10 illustrate another exemplary embodiment.
Figure 10:
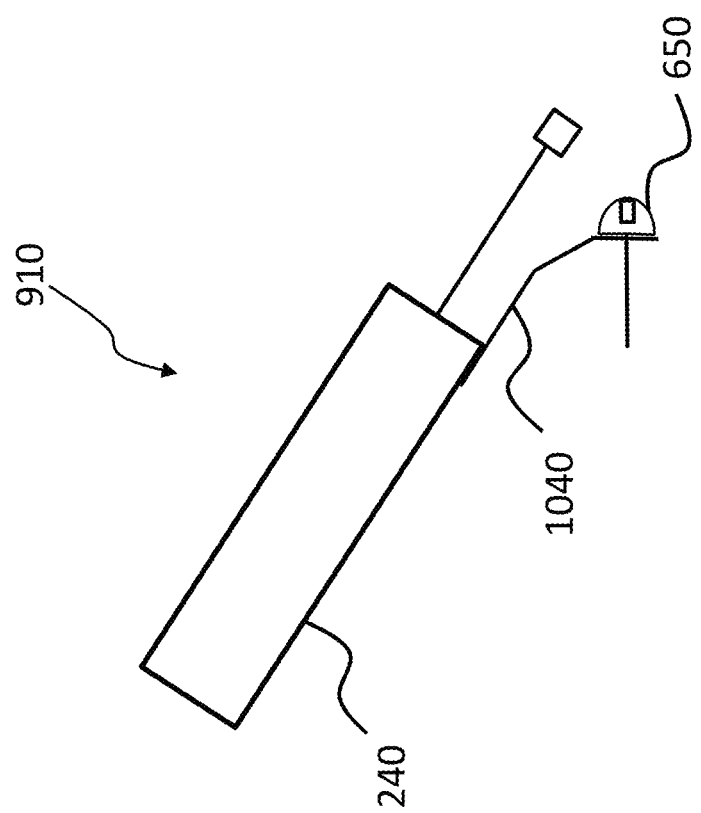

As noted above, in some embodiments, the implantable apparatus includes a transducer that is a middle-ear actuator that includes a force output portion. An exemplary embodiment of this is implantable apparatus 910 of FIGS. 9 and 10, which includes actuator 240 (corresponding to actuator 240 of FIGS. 2A and 2B). FIG. 10 depicts fixation mechanism 1040, which is a fixation mechanism configured to be fixed to the wall of the middle ear cavity between the tympanic membrane and the opening of the passageway 219 as can be seen in FIG. 9. Also, as can be seen, fixation mechanism 1040 includes a plurality of compound sections is also noted that the alignment of fixation mechanism 1040 in FIG. 9 generally corresponds to the alignment of the transducer positioning mechanism of FIG. 8A above. That is, in an exemplary embodiment, the transducer positioning mechanism of FIG. 8A is a mechanism configured to be attached at about the same location as the fixation mechanism 1040 of FIG. 9. It is also noted that in some embodiments, the positioning mechanism of FIG. 8A can be attached to other locations of the wall of the middle ear cavity. In some embodiments, the fixation mechanisms detailed herein (which also includes the positioning mechanism of FIG. 8A, as that is a fixation mechanism as well) are configured to be attached to any location of the wall of the middle ear cavity provided that such can enable the teachings detailed herein.

As can be seen, the fixation mechanism of FIGS. 9 and 10 include a fixation arm that extends away from the force output portion of the actuator, and the fixation arm is configured to be secured to the recipient in the middle ear cavity of the recipient. As with the embodiments detailed above with respect to the microphone, in these embodiments, at least a portion of the actuator 240 is located in the passage through the bone to the middle ear cavity outside the middle ear cavity (it is noted that the term "middle ear cavity" as used herein refers to the natural cavity, and thus excludes any portion of the passageway).

In some exemplary embodiments, the force output portion is a membrane to which the coupling mechanism 248 is connected. Indeed, in some exemplary embodiments, the actuator is for all intents and purposes identical to the tube microphone detailed above (and thus can be considered to be a "tube actuator"), except that it it's principle of operation is reversed out of the microphone. That said, in some alternate embodiments, there is no membrane at the end of the housing of the actuator, and instead the coupling mechanism reciprocally sides through a seal in the housing, thus making the arm of the coupling mechanism the output portion of the actuator.

Figure 11:
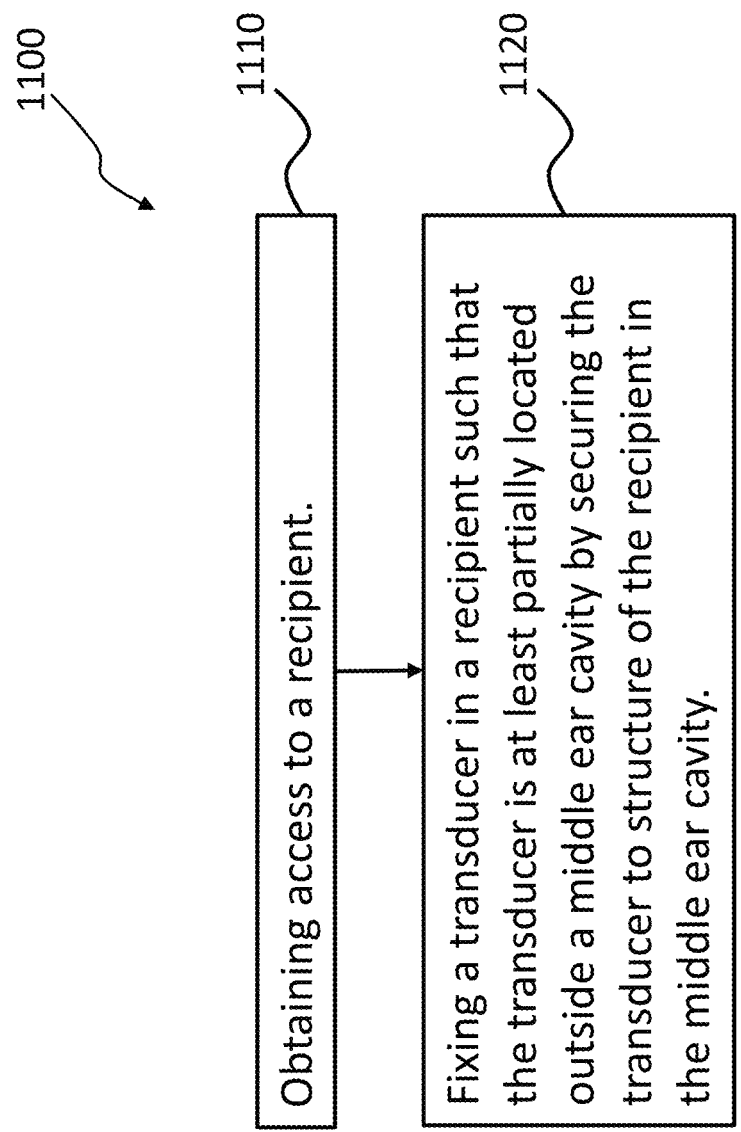
FIG. 11 presents an exemplary flowchart according to an exemplary method.
Figure 12:
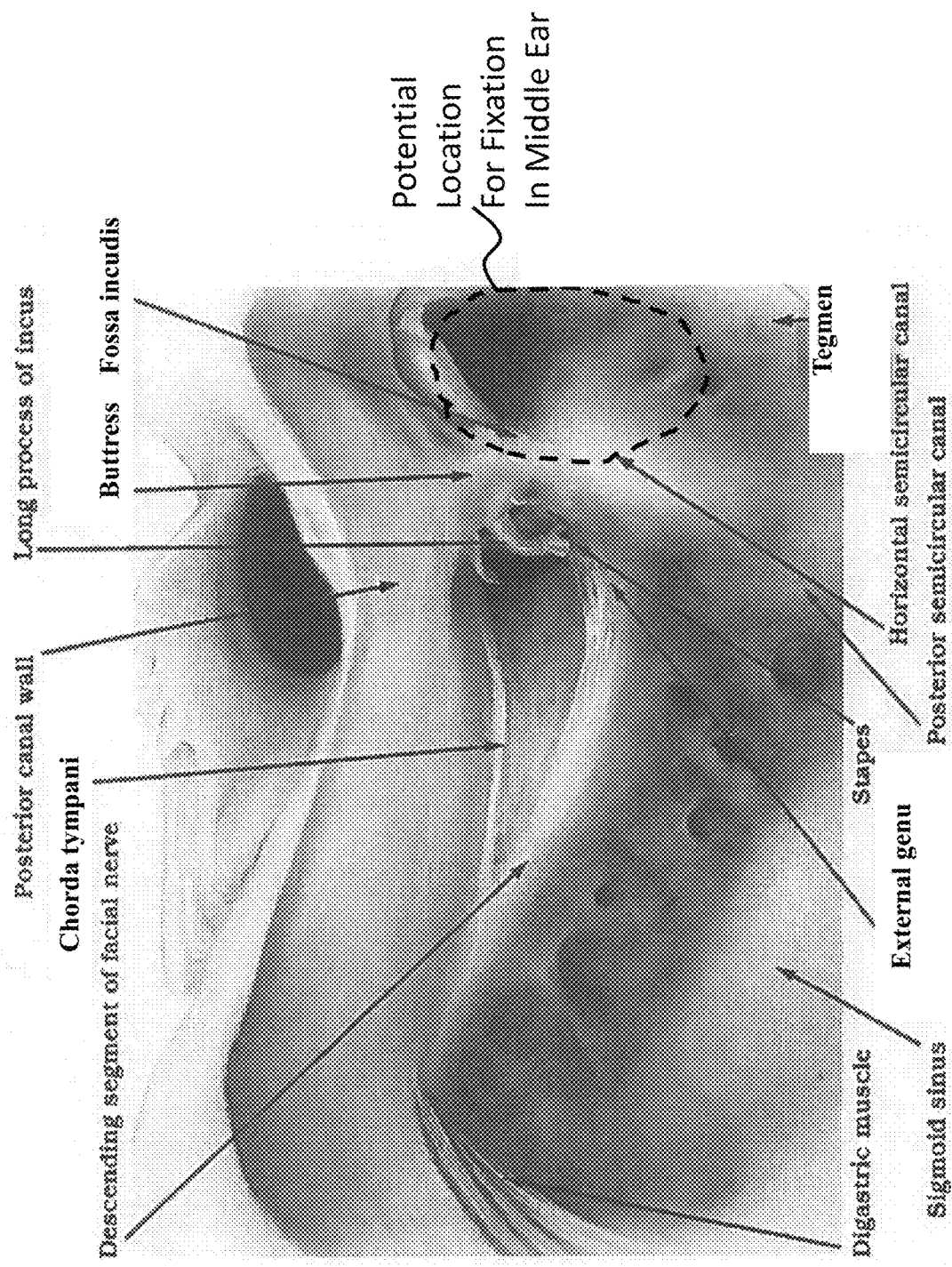
FIGS. 12-16 present exemplary schematics depicting exemplary potential locations for fixation of the fixation apparatus in the middle ear cavity.
Figure 13:
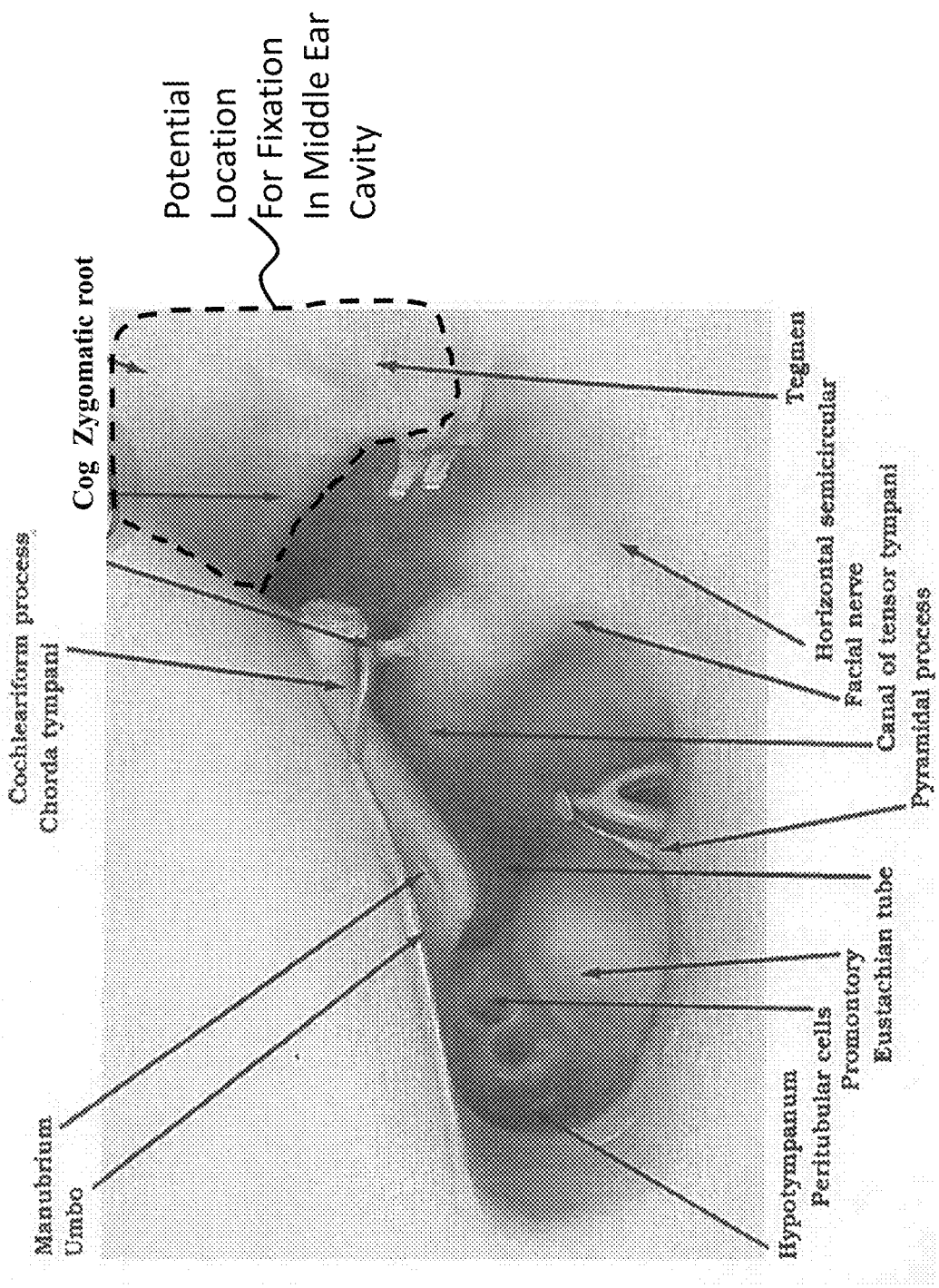
Figure 14:
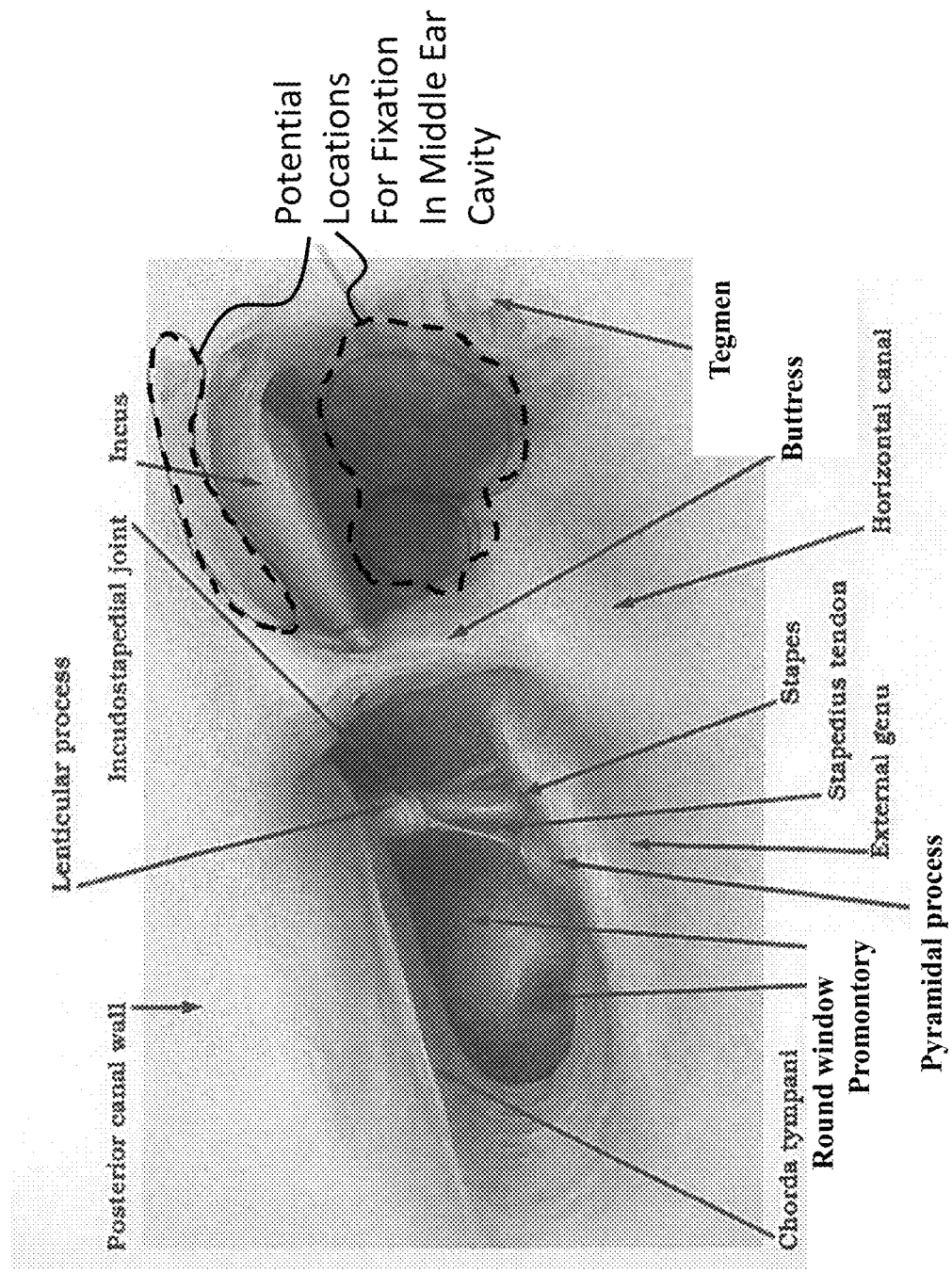
Figure 15:
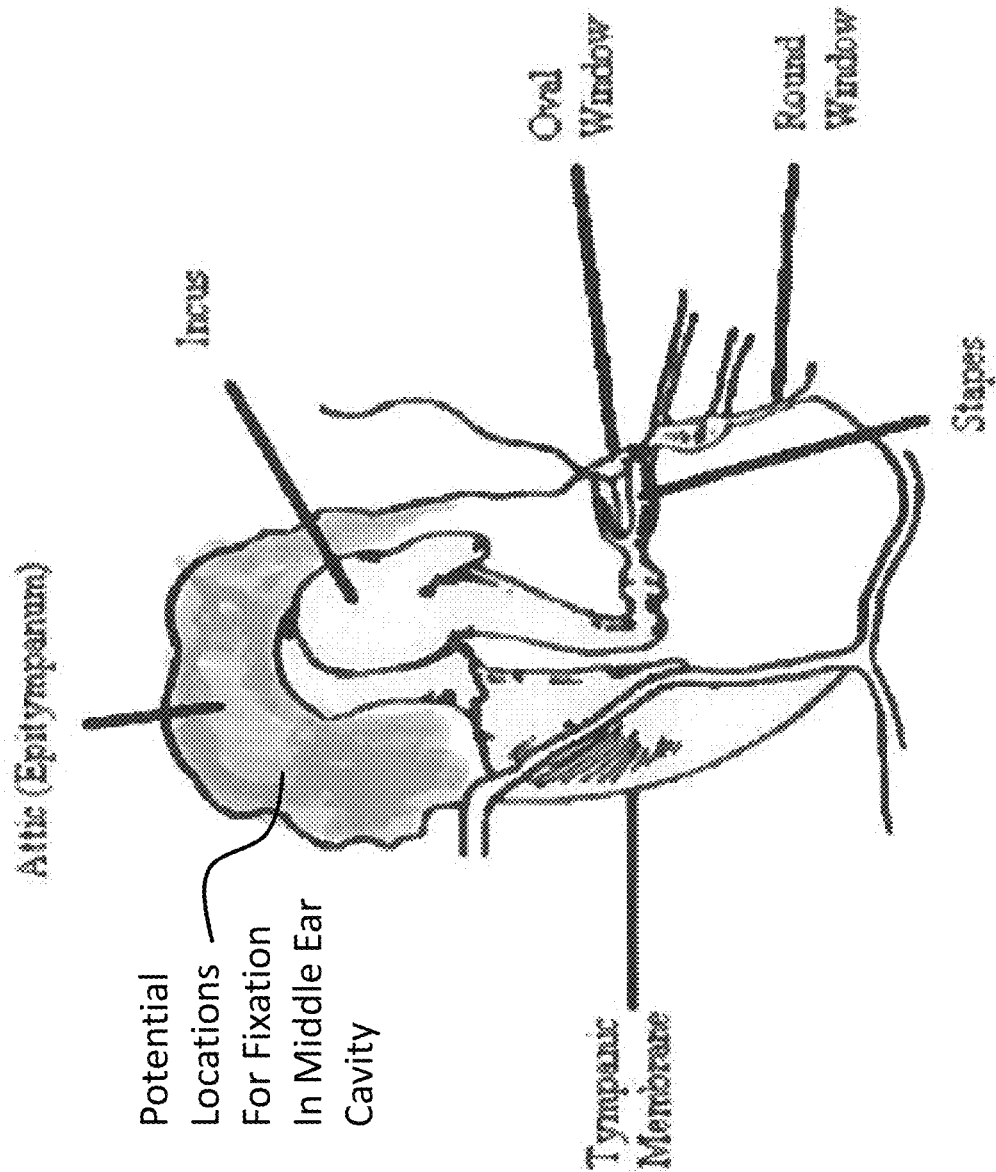
Figure 16:
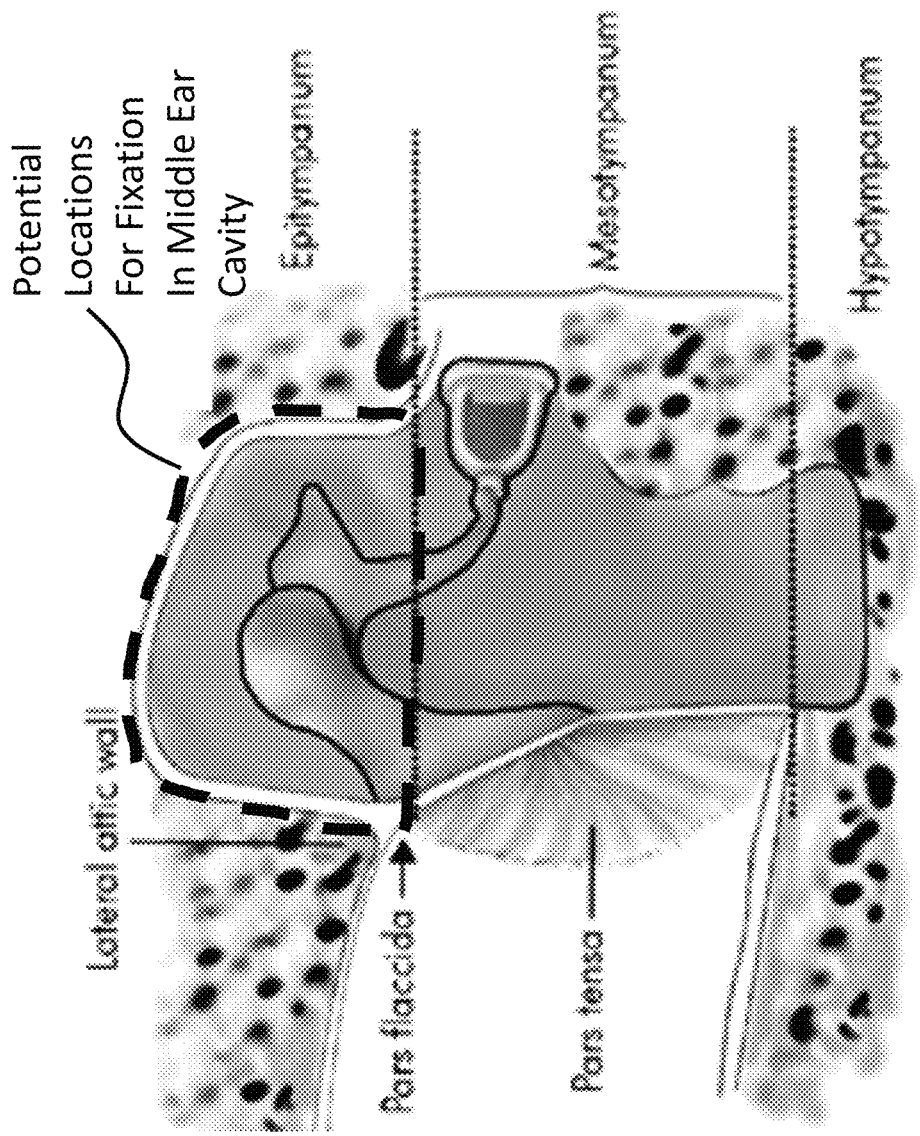

In view of the above, it can be seen that an exemplary embodiment can include a method. In this regard, FIG. 11 presents an exemplary flowchart for a method, method 1100, which includes method action 1110, which includes obtaining access to a recipient. In the embodiment of method 1100 of FIG. 11, the method includes method action 1120, which includes fixing a transducer in a recipient such that the transducer is at least partially located outside a middle ear cavity by securing the transducer to structure of the recipient in the middle ear cavity. With respect to the teachings detailed above, in an exemplary embodiment, the structure of the recipient in the middle ear cavity can be the wall(s) of the middle ear cavity. In an exemplary embodiment, the structure can be the outside of the cochlea, although such may not necessarily have the maximum utilitarian value that would be desired. Any structure within the middle ear cavity that can support the transducer or otherwise utilized to fix the transducer according to the teachings detailed herein can be utilized in at least some exemplary embodiments.

In an exemplary embodiment, the structure of the middle ear to which the fixation mechanism can be fixed can be, by way of example and not by limitation, the chorda tympani, the incus buttress, the fossa incudis, the wall on the opposite side of the mastoid tip, the facial nerve, the external genu, the buttress, the tegmen, the pyramidal process, the cog, etc.

FIGS. 12-16 present exemplary locations for potential fixation of the fixation mechanism in the middle ear. The recipient structure in the background of the areas inside the annotated dashed lines is locations where the bone screw can be located. Also, as will be detailed below, in some embodiments, there is no bone screw. Thus, these are all areas where some form of reaction force can be applied (glue, tension, compression, etc.—again, more on this below) to fix the fixation mechanism in the middle ear.

By "the transducer is at least partially located outside a middle ear cavity," it is meant that at least a portion of a component recognizable as the transducer if reduced to the fewest number of components (e.g., no wires to/from the housing 248, no holing fixture, etc.) is located outside the middle ear cavity.

Concomitant with the teachings above, as a result of method 1100, in some embodiments, the transducer is at least partially located in an artificial passageway through a temporal bone of the recipient upon fixing the transducer. Also concomitant with the teachings above, in some embodiments, a fixation component is utilized to fix the transducer, wherein upon completion of the action of fixation, the fixation component extends from a wall of the middle ear cavity to the transducer so as to fix at least a portion of the transducer in the artificial passageway.

Also, in some embodiments, upon completion of the action of fixation, no part of the fixation component or the transducer is fixed to a wall of the artificial passageway and, in some embodiments, additionally, no part of the fixation component or the transducer is fixed to an outer surface of the mastoid bone. (An outer surface of the mastoid bone is the surface of the temporal bone (e.g., the outer surface of the mastoid bone facing the outside of the recipient/skin of the recipient that grows mammalian hair).) An exemplary embodiment of this is depicted in FIG. 19, where fixation mechanism 1910 is fixed using bone screw 650 to the outer surface of the mastoid bone.

Figure 19:
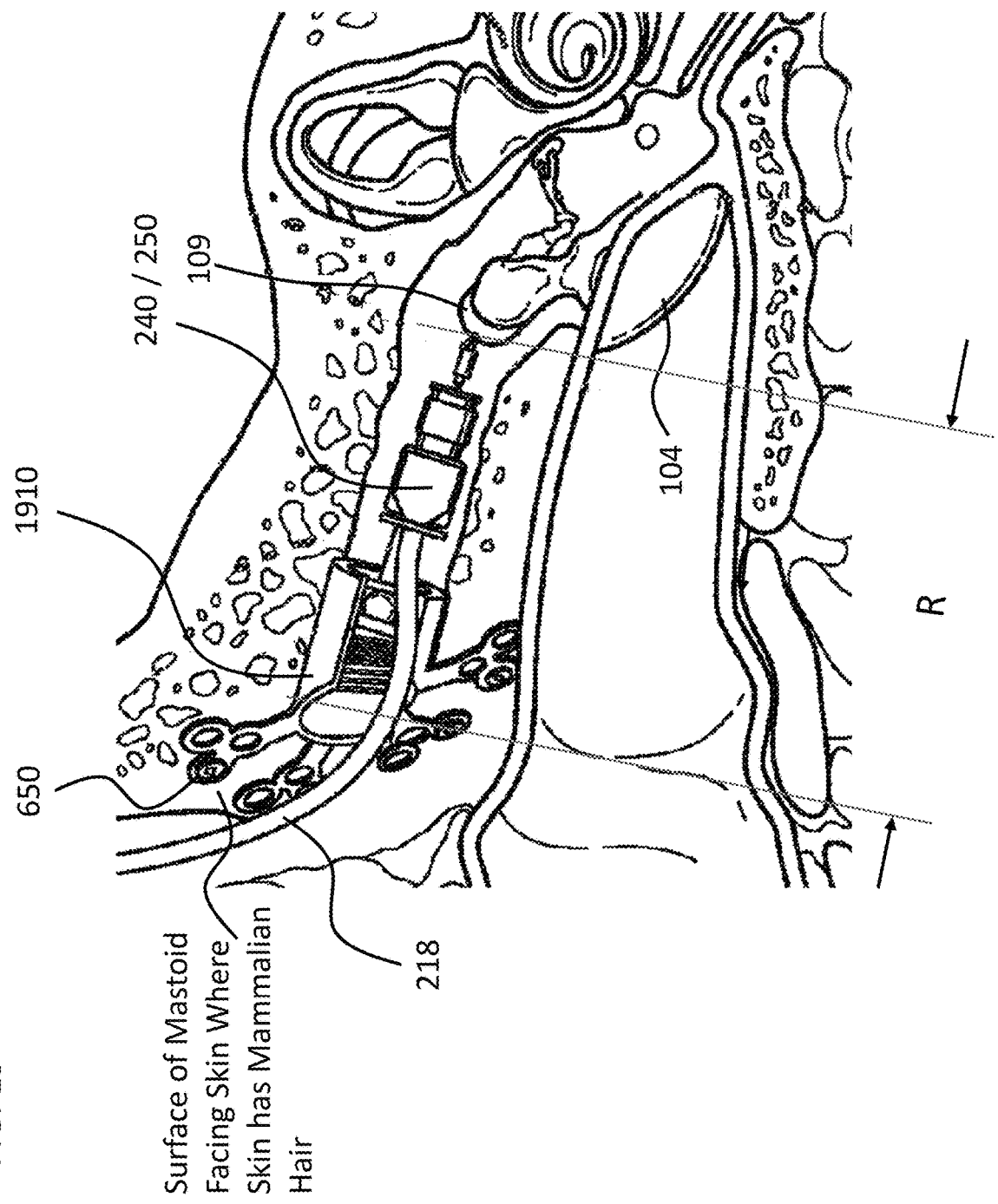
FIG. 19 represents an alternate arrangement for fixing a transducer in a recipient.

It is noted that in some embodiments, as seen above, an electrical lead assembly (e.g., lead assembly 218 as seen in FIG. 19) can extend from the transducer to the surface of the mastoid bone through the passageway to a stimulator, where the stimulator can be fixed to the mastoid bone, such as at the surface of the mastoid bone, but this does not corresponds to a component that fixes the transducer, as the cable/lead assembly is at most acting like a tether (if the transducer were otherwise free), and thus there is no fixation in this scenario.

With respect to embodiments such as those detailed above with respect to FIGS. 6, 6A, and 8, by way of example, upon completion of the action of fixation, the at least a portion of the transducer is supported in the artificial passageway via at least a quasi-cantilever regime. That is, the fixation mechanism can be a pure cantilever system, or can be a system that can be modeled as if it was a cantilever beam with minimal error/deviation from the actual system.

Figure 17:
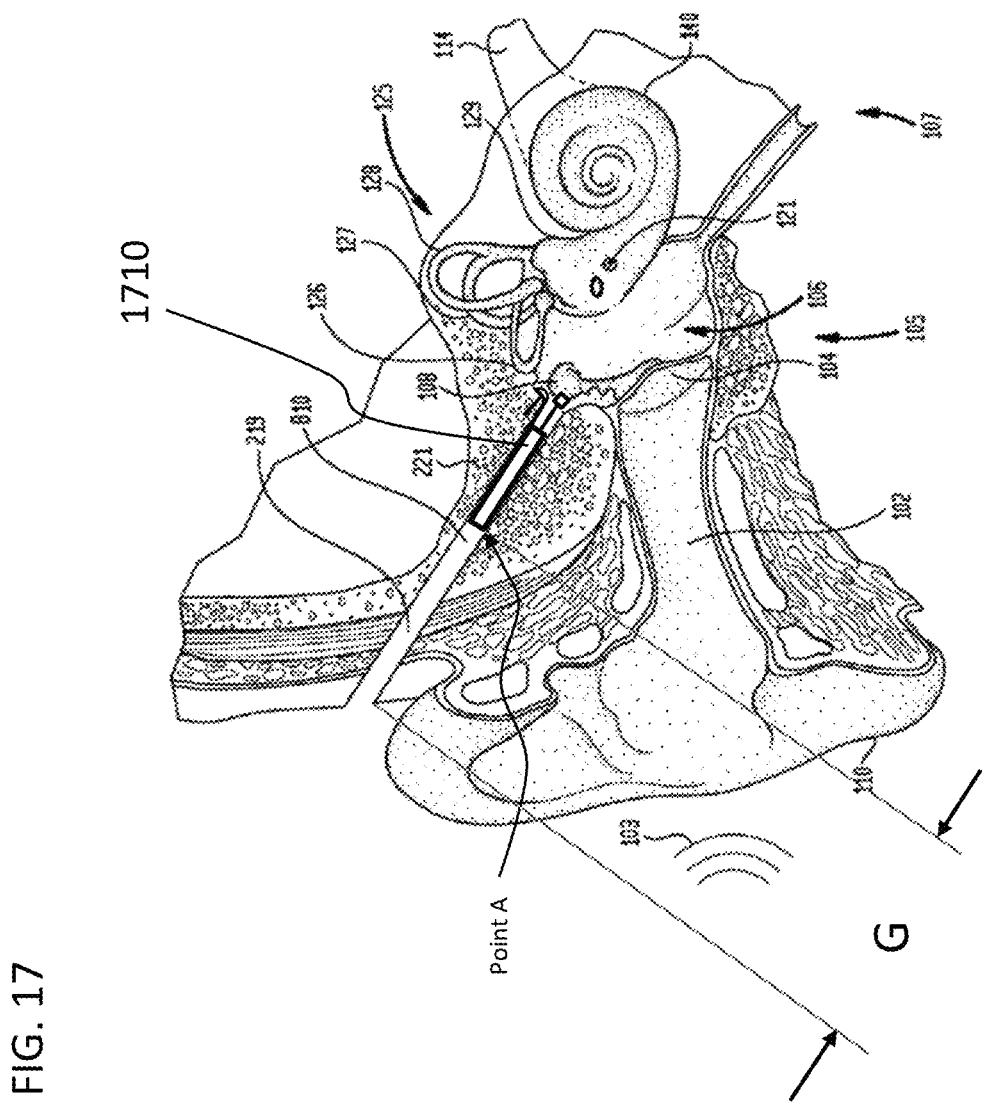
FIGS. 17 and 18 schematically represent growth of a skull.
Figure 18:
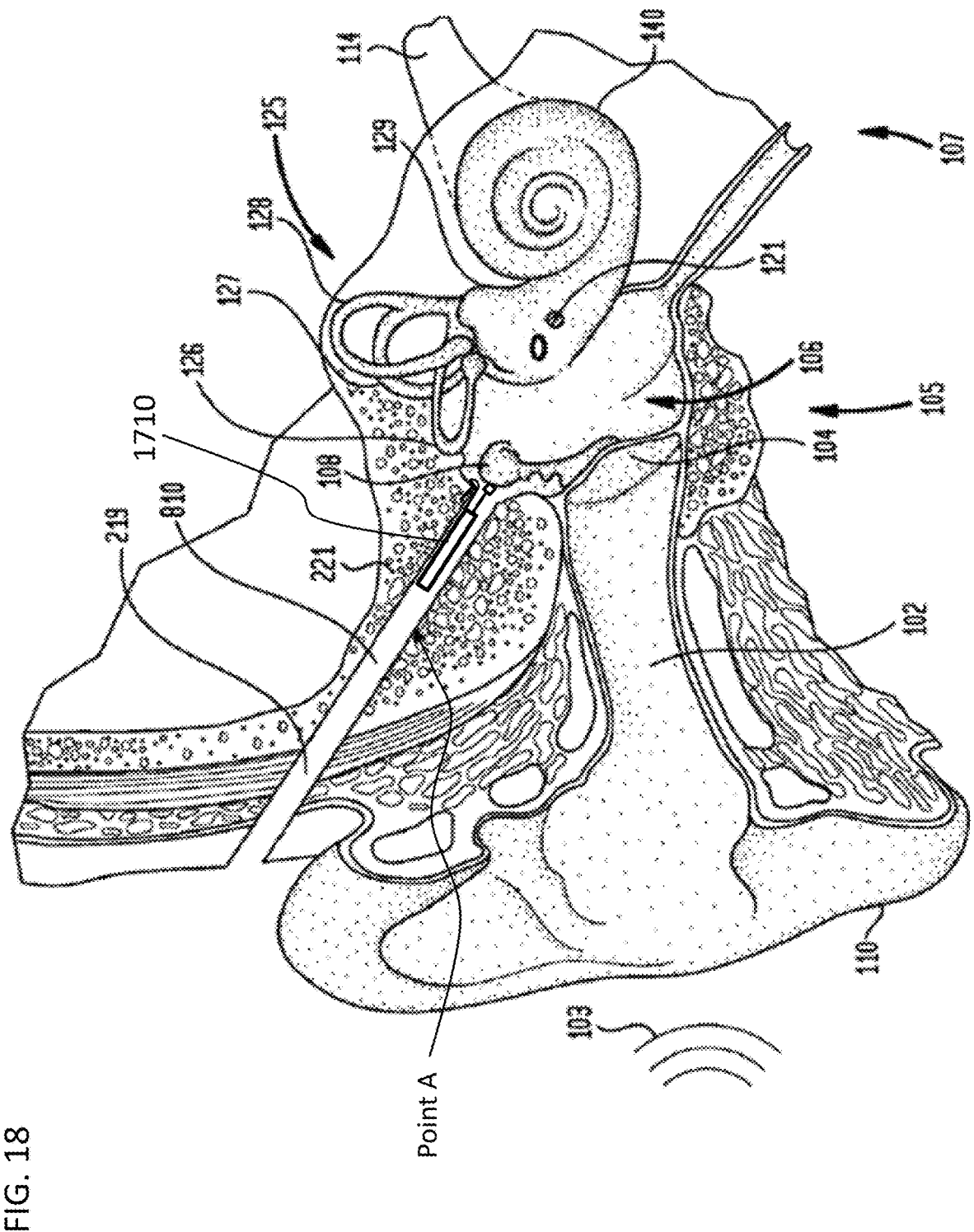

Also concomitant with the teachings above, such as the embodiment of FIG. 8A, in an exemplary embodiment, upon completion of the action of fixation, the transducer can be controllably moved in the artificial passageway. This can be under the control of a powered actuator for powered movement or by manual movement (with or without a tool). Moreover, in some exemplary embodiments, upon completion of the action of fixation, portions of the artificial passageway surrounding the transducer can move in a longitudinal direction relative to the transducer due to growth without causing the transducer to move. In this regard, FIGS. 17 and 18 depict by way of conceptual representation only the growth of the skull of a recipient from temporal location A (e.g., childhood) to temporal location B (e.g., post adolescence) in a one G environment, where FIG. 17 conceptually represents the size of the skull and the location of the implantable apparatus 1710 at temporal location A, and FIG. 18 conceptually represents the size of the skull and the location of the implantable apparatus 1710 at temporal location B. As can be seen, the size of the skull has enlarged between the two temporal locations. The length of the passageway 219 has both lengthened and has expanded in the axial direction (the diameter has increased). Accordingly, as can be seen, midpoint 810 of passageway 219 (the midpoint between the outer opening of the passageway 219 and the inner opening of the passageway 219 has moved away from the implantable apparatus 710 in general, and from the rearmost location of the implantable apparatus 710 in particular. (It is briefly noted that the figures of 17 and 18 are but conceptual. In reality, the middle ear cavity does not enlarge as much, as at all, relative to the enlargement of the other portions of the skull. Indeed, in an exemplary embodiment, from temporal location A to temporal location B (and, with respect to the arrangement of FIG. 19, dimension R, which is measured from the surface of the mastoid bone/opening of the passageway, to the location where the implantable component working end is attached to the ossicles when the system is at rest—where the performance of this hypothetical system vis-à-vis growth can be compared to that of the other embodiments herein vis-à-vis movement due to growth from the point where the working end is attached to the ossicles) the length and/or the diameter of the passageway 219 increases by at least or by no more than 10, 20, 30, 40, 50, 60, 70, 80, 90, 100, 125, 150, 175, 200, 225, 250, 275, 300, 325, 350, 375, 400, 425, 450, 475, 500 percent, or more or increases by any value or range of values therebetween in 1% increments (at least 77%, no more than 188%, increases by 52% to 222%, etc.) than the increase in the maximum diameter of the inner ear cavity 106 from temporal location A to temporal location B. In an exemplary embodiment, temporal location A and B is separated by or at least by 1, 2, 3, 4, 5, 6, 7, 8, 9, 10, 11, 12, 13, 14, 15, 16, 17, 18, 19, or 20 years, or any value or range of values therebetween in 1 day increments. Thus, in an exemplary embodiment, Because the fixation mechanism of the implantable apparatus is configured to be fixed to the wall of the middle ear cavity of the recipient, as the skull grows from temporal location A to temporal location B, because the growth of the middle ear cavity is relatively de minimis during that time period, the position of the implantable apparatus in general, and the transducer thereof in particular, relative to the anatomical structure of significance (e.g., bone 108, the tympanic membrane 104, in the case of an actuator—the oval window, the stapes, etc.) relatively little, if at all, at least as compared to that which would be the case if the implantable apparatus was fixed to the inner wall of the passageway 219 and/or the implantable apparatus was fixed to the outer surface of the mastoid bone (the surface opposite the middle ear cavity 106—the surface that faces the skin that grows mammalian hair).

Accordingly, in an exemplary embodiment, method 1100 is practiced where the recipient is in adolescence or pre-adolescence and portion of the recipient where the transducer is at least partially located is subject to growth movement relative to the transducer. By way of example only and not by way of limitation, the portion of the recipient where the transducer is at least partially located can be the passageway 219 in general, and the wall of the passageway 219 in particular.

Still further, in an exemplary embodiment of method 1100, method 1100 is practiced where the recipient is less than C years old and a portion of the recipient where the transducer is at least partially located is subject to growth movement relative to the transducer. In an exemplary embodiment, C is 1, 2, 3, 4, 5, 6, 7, 8, 9, 10, 11, 12, 13, 14, 15, 16, 17, 18, 19, or 20, or any value or range of values therebetween in 0.01 increments.

Thus, in view of the above, it can be seen that in some embodiments, there is an implantable apparatus, comprising an implantable transducer fixation mechanism, the fixation mechanism being configured to receive an implantable transducer, and a middle ear transducer, wherein the middle ear transducer is incompatible with complete placement in a middle ear. The transducer and the fixation mechanism can be any of those detailed above and/or variations thereof and/or any other type of device that can enable the teachings detailed herein. In this exemplary embodiment, the implantable transducer fixation mechanism is a growing child compatible fixation mechanism, such as those detailed above with respect to FIGS. 5-10. This as opposed to, for example, the arrangement of FIG. 19, where, upon growth of the skull, the fixation mechanism will move to the left relative to the middle ear cavity, and thus the transducer 240/250 will be pulled away (to the left) away from the middle ear cavity, and thus could potentially require repositioning, which could require an additional surgery to access the transducer.

Consistent with the teachings above, the fixation mechanism includes a fixation arm that extends away from the transducer at an oblique angle relative to a longitudinal axis of the transducer. Again, the fixation arm can be an integral part of the housing or other component of the transducer (e.g., welded to the housing, a monolithic portion of the housing, etc.). Alternatively, the fixation arm can be part of a component that grips or otherwise is releasably attached to the transducer (e.g., one that cradles the transducer).

Figure 20:
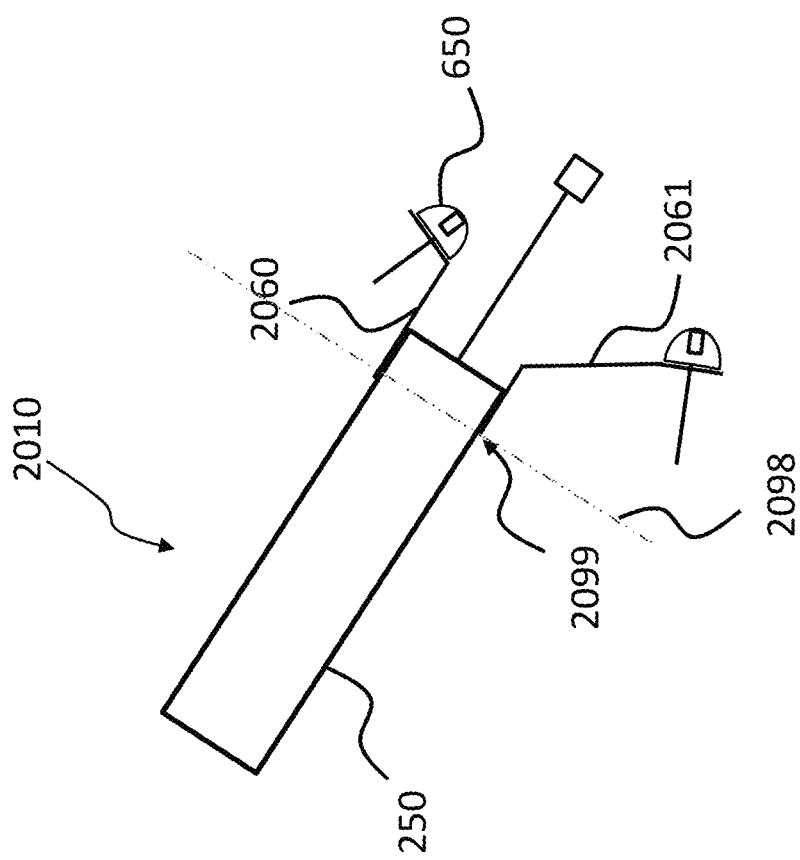
FIGS. 20 and 21 present alternate exemplary embodiments.
Figure 21:
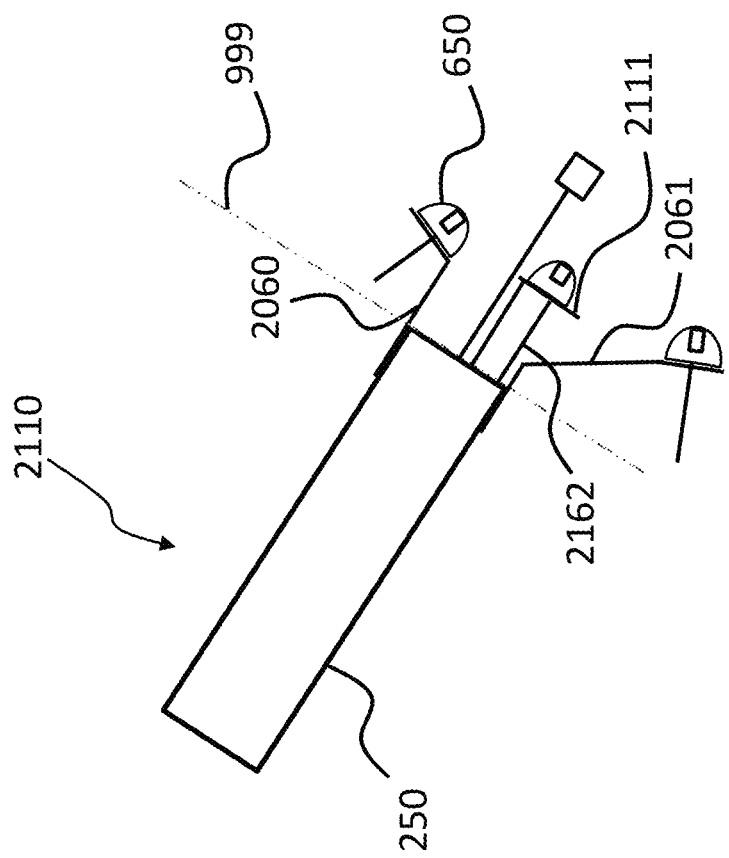

FIG. 20 depicts an exemplary embodiment where the fixation mechanism includes at least two fixation arms 2060 and 2061 that extend away from the transducer to enable a two point fixation regime inside the middle ear cavity. The embodiment of FIG. 20 depicts the two fixation arms welded to the transducer 250. In an alternate embodiment, the two fixation arms are monolithic components of the housing of the transducer 250. In an alternate embodiment, the two fixation arms are attached to a ring, such as the ring detailed above in FIG. 8, and the transducer is attached to the ring (screw fit, welded, etc.). Still further, in an exemplary embodiment, the fixation mechanism includes at least three fixation arms that extend away from the transducer to enable a three point fixation regime inside the middle ear cavity. This is seen in FIG. 21, where the implantable apparatus 2110 includes arm 2162 which corresponds to an additional arm relative to the embodiment of FIG. 20. As can be seen in FIG. 21, arm 2162 includes portions that are of different cross-sectional width. As can be seen, there is a portion 2111 that is wider relative to the portion of armed 2162 that is closest to the housing of transducer 250. This wider portion provides additional space for the bone screw.

It is noted that while the embodiments of the arms have been presented in terms of elongate plates, in some alternate embodiments, the arms are cylindrical structures. In some embodiments, the arms are wires that have sufficient strength both with respect to tension and compression to hold the transducer in place. Any arrangement of the implantable fixation mechanism that can enable the teachings detailed herein can be utilized in at least some exemplary embodiments.

Consistent with the teachings above, the fixation mechanism is configured such that at least a portion of the fixation mechanism is located outside the middle ear cavity in an artificial passageway through the temporal bone when the fixation mechanism supports the transducer and the passageway. Still further, the fixation mechanism is configured to enable the temporal bone to grow as the recipient child grows to adulthood (or the generic recipient grows) while limiting a movement of a point on the fixation mechanism furthest away from the middle ear cavity and proximate the transducer and located outside the middle ear cavity when implanted in the recipient (this location would be the location indicated by arrow 2099 in FIG. 20) to no more than M % of the relative movement of the nearest recipient structure to the point (which would likely be, in the embodiments disclosed herein, a point along the plane 2098 that first intersects with the inner diameter of the passageway 219. In an exemplary embodiment, M is 0, 0.25, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, or 75%, or any value therebetween in 0.1% increments.

Figure 22:
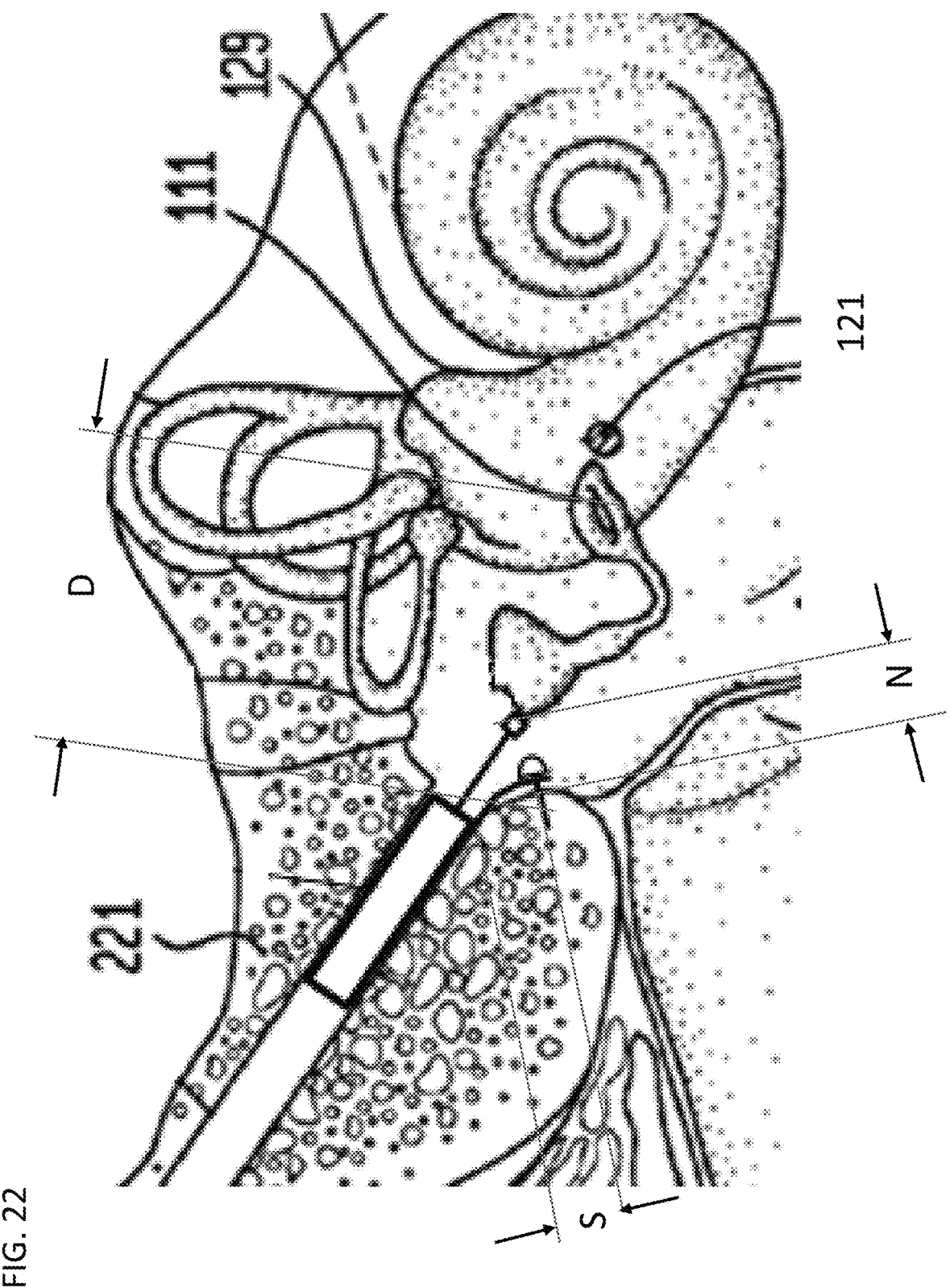
FIG. 22 presents exemplary details of an exemplary embodiment.

In an exemplary embodiment, the transducers detailed herein are part of an assembly that is configured at a first connection location to be mechanically coupled to one of a middle ear bone (one of the ossicles) or a window of a cochlea at a first connection point to enable mechanical energy transfer thereat. In this exemplary embodiment, the fixation mechanism is configured at a second connection location to be mechanically coupled to a wall of the middle ear to fix the fixation mechanism to the middle ear, and a shortest distance between the first connection point and the second connection point when the implantable apparatus is in free space and unrestrained is less than or equal to N, where N can be 0.5, 0.75, 1, 1.5, 2, 2.5, 3, 3.5, 4, 4.5, 5, 5.5, 6, 6.5, 7, 7.5, 8, 8.5, 9, 9.5, or 10 mm, or any value or range of values therebetween in 0.1 mm increments. FIG. 22 depicts an exemplary scenario of N. It is noted that the distances are measured from the bone/tissue of the recipient where the fixation structure first enters into the surface, or more accurately, an extrapolated surface (as the surface is removed for the bone screw), at a tangent plane at the geometric center of the opening formed by the bone screw. N would be different for the embodiment of FIG. 5 vs. FIG. 9, etc., owing to the different respective fixation locations, etc.

The embodiments of FIGS. 5-10, 17, etc., are embodiments where the fixation mechanism is configured to fix the transducer to the recipient via fixation components only located in the middle ear (e.g., the bone screws located in the middle ear cavity). This as opposed to an embodiment where there is, for example, a bone screw in the passageway 219 or on the surface of the mastoid bone (such as is the case with respect to the arrangement of FIG. 19). Note again that, for example, even if in the embodiments of FIGS. 5-10, 17, etc., there is a cable/electrical lead extending from the transducer to a stimulator or the like located on the surface of the mastoid bone, where the stimulator is fixed to the surface of the mastoid bone, that is still an embodiment where the fixation mechanism is configured to fix the transducer to the recipient via fixation components only located in the middle ear, because the cable does not fix the transducer to bone or to the recipient.

Figure 23:
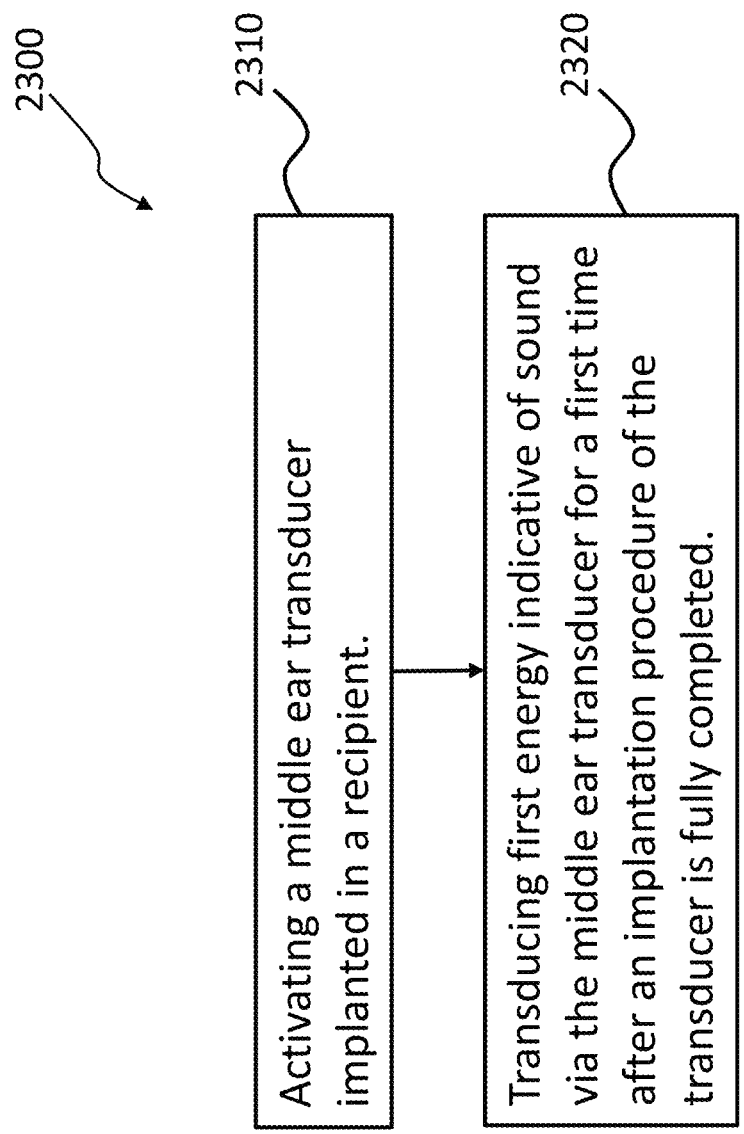
FIGS. 23-25 present exemplary flowcharts for some exemplary methods.

FIG. 23 depicts a flowchart for an exemplary method, method 2300, according to an exemplary embodiment. Method 2300 includes method action 2310, which includes activating a middle ear transducer implanted in the recipient. By activating, this is meant turning the transducer on/providing an electrical current to the transducer, providing an inductance coil to the implanted inductance coil (e.g., by placing the external inductance coil adjacent to the skin of the recipient above the implanted coil), etc., but not necessarily utilizing the transducer to transduce energy (e.g., this could be in a stand-by state). Any action that will place the transducer into a state where it is usable relative to that which was the case prior to method 2310 can be used to execute method action 2310.

Method 2300 further includes method action 2320, which includes transducing first energy indicative of sound via the middle ear transducer for the first time after an implantation procedure of the transducer is fully completed. By "transducing first energy indicative of sound via the middle ear transducer," this means both (i) the transduction of electrical signals that is based on sound (e.g., sound captured by the microphone of the hearing prosthesis, etc.) by an actuator to output mechanical energy, and (ii) the transduction of sound energy utilizing a microphone to output electrical signals. That is, method action 2320 can be executed utilizing an actuator or a microphone.

With respect to the feature that method action 2320 is executed for the first time after an implantation procedure of the transducer is fully completed, this means that this is an actual use of the transducer post-operative/beyond testing of the device during surgery or proximate surgery. Note also that this is "a first time," which means that it is generic, and thus need not be the first time (as opposed to "the first time"), although in some exemplary embodiments, a first time is indeed the first time.

Method action 2320 constitutes a normal use of the transducer, as opposed to an action that might occur during surgery. For example, by way of example only and not by way of limitation, in an exemplary embodiment, action 2320 is executed after all of the following actions have been completed:

Ear Canal and Setup
 Myringotomy tray—Clean EAC and inspect drum,
 Prep postauricular skin and mark incision as below, local anaesthetic
 Drape as for mastoid+separately drape pinna anteriorly to keep EAC separate from mastoid
Soft-Tissue Work
 Postauricular incision with superior limit 3 cm up from root of helix, and down to level drawn from inferior canal wall 1 cm behind postauricular sulcus.
 Stepped fascial incision onto bone to create broad anteriorly based flap Elevate flap fully to allow room for fixation device behind cortical mastoidectomy.
Mastoidectomy
 Keep distance between sinodural angle and EAC small—no need to expose dura or sigmoid—mark likely central screw point 25×25 from centre of EAC.
 If necessary for landmarks identify dura anterosuperiorly
 Thin the posterior canal wall all the way down particularly medially and expose the incus body broadly
 Ensure EAC wall drilling creates parallel surface to the body of the TubeMic when positioned on incus.
Fixation Device
 When identifying correct position on mastoid cortex loosen the ball bearing so it holds but can be moved easily first (yellow screwdriver)
 Place the microphone holder pointing above the incus, then guide the "Codacs dummy actuator without incus" to correct distance then readjust the holder. The body of the TubeMic should be clasped at its midpoint and the body or clasp should contact the posterior canal wall.
 Place central screw first followed by at least one screw in each of the 3 main arms.
 Tighten all screws
Coupling
 Pass TubeMic through fixation device clasp and advance balltip so it is sitting tension free within the drilled incus recess. The TubeMic wire can be bent+−15 degrees to allow correct positioning.
 If using cement avoid cement touching the buttress
 Ensure the surfaces to be cemented are completely dry.
 The cement should cover the ball of the TubeMic so that no part is visible but without excessive cement. As a guide apply 0.5 mm×0.5 mm ball of cement positioned on slightly curved needle
 If using OtoMimix an entire vial of powder should be mixed with the liquid to ensure the correct consistency, mixed for 3 minutes
 Allow to dry for 14 minutes before any testing is carried out.
Closure
 Skin closure
Dressing
 Head bandage
Patient Removed from Operating Room
 Patient sent to recovery room.
Dressing Removal after Healing
 Removal of final head bandage (if changed after the initial head bandage).

Variations of the above can be present as well in some embodiments.

Note also that action 2320 can be executed 10, 20, 30, 40, 50, 60, 70, 80, 90, 100, 110, 120, 130, 140, 150, 160, 170, or 180 or more days after the implantation procedure is fully completed.

In an exemplary embodiment of method 2300, the middle ear transducer is located at least partially outside the middle ear cavity, and the middle ear transducer is only fixed to structure inside the middle ear cavity, concomitant with the teachings above.

Figure 24:
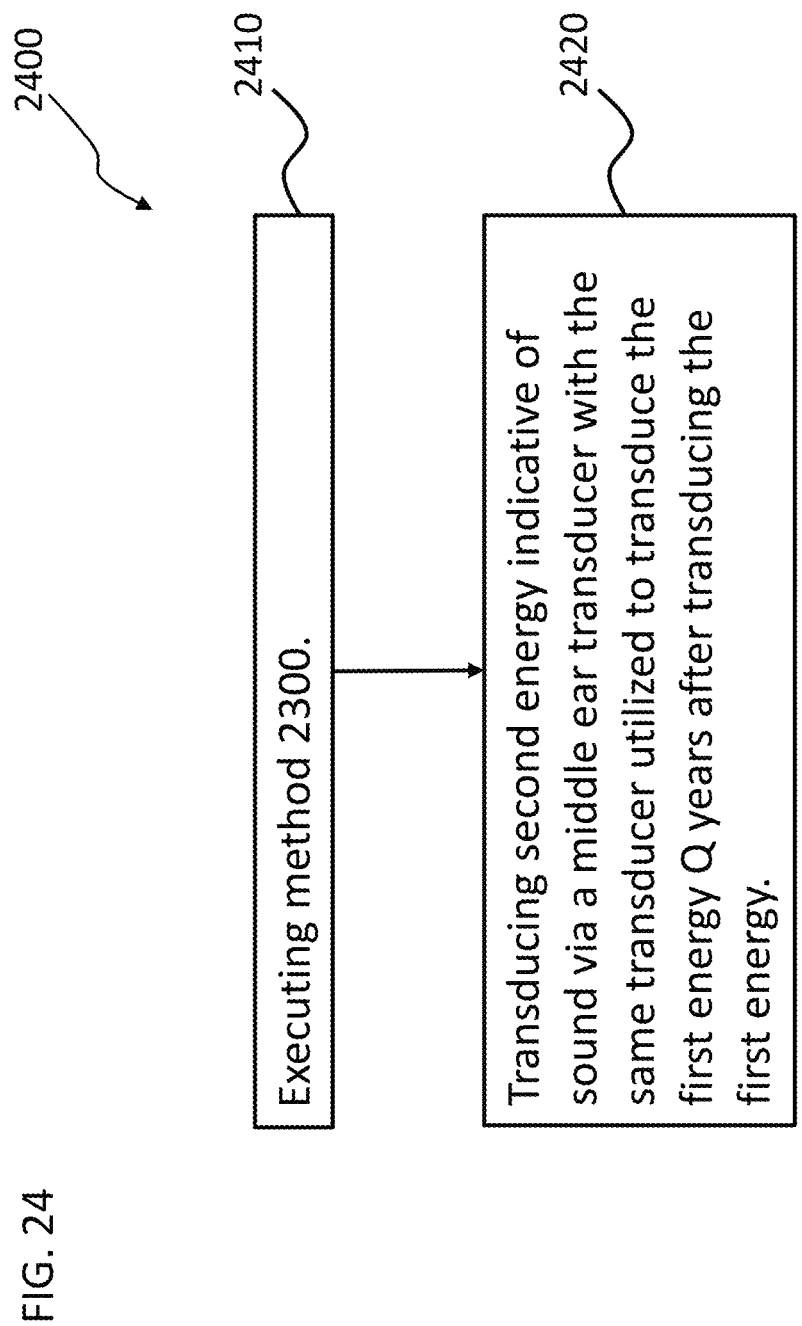

FIG. 24 presents another exemplary flowchart for an exemplary method, method 2400, which includes method action 2410, each includes executing method 2300, or at least a part of such (e.g., method action 2320). Method 2400 further includes method action 2420, which includes transducing second energy indicative of sound via a middle ear transducer with the same transducer utilized to transduce the first energy Q years after transducing the first energy. In an exemplary embodiment, Q is 0.25, 0.5, 0.75, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15 or any value or range of values therebetween in 0.01 increments. In an exemplary embodiment of method 2400, the action of transducing first energy indicative of sound via a middle ear transducer is executed in an adolescent or a pre-adolescent before completing full growth. In an exemplary embodiment, the adolescent or pre-adolescent is 1, 2, 3, 4, 5, 6, 7, 8, 9, 10, 11, 12, 13, 14, 15, 16, 17, 18, 19, 20, 21, or 22 years old (as one of ordinary skill in the art would consider such—a 14 month old is considered 1 year old, as is also the case with a 23 month old, etc.) or any value or range of values therebetween in one day increments.

In the exemplary embodiment of method 2400, a point on bone of the recipient proximate the transducer has moved significantly due to growth relative to the transducer since method action 2320 was executed. By way of example, such point can be the middle point 810 of the passageway 219 (if such is proximate the transducer, depending on the embodiment), the point closest to the mastoid surface-most portion of the transducer when method action 2320 is executed (point A in FIGS. 17 and 18), the point furthest from the mastoid surface of the transducer, the point closest to the center of gravity of the transducer, etc. Any point proximate the transducer can be used in some embodiments.

Further, in method 2400, the position of the transducer relative to the oval window of the cochlea is at least effectively the same as that which was the case when the first energy was transduced, and no intervening surgery occurred between the first and the second energy transductions to relocate the transducer and/or no movement of the transducer via a positioning system has occurred to compensate for movement of the point on the bone between the first and second energy transductions. FIG. 22 depicts an exemplary distance D between the transducer and the oval window (eclipsed by bone 111), where the distances have been measured from the closest point of the transducer to the oval window to the geometric center of the oval window. However, in other embodiments, other reference points can be used, providing that the reference points are consistent over the temporal period spanning Q.

In an exemplary embodiment of method 2400, the idea is that the adolescent or preadolescent child can grow, and thus the child's skull can grow, but the positioning of the transducer does not move relative to the oval window in a meaningful manner. Conversely, if the distance D changed in a manner that was not effectively the same as that which was the case at the beginning of the temporal period spanning Q, in at least some exemplary embodiments, the transducer position would have to be re-adjusted and/or the linkage between the transducer and the components of the recipient to which the output of the transducer is attached (e.g., the ossicles in FIG. 22) would have to be adjusted, because the change in location would provide a "pre-load," potentially, on the transducer, at least a pre-load for which was not originally accounted (some are already pre-loaded by design), or could even potentially prevent the transducer from operating in the first instance (e.g., the output arm (or output wire) is "pulled" relative to the transducer so far out that it is at the end of its maximum stroke, and thus cannot reciprocate, etc.).

In an exemplary embodiment, movement of the position of the transducer relative to the oval window of the cochlea that results in something more than that which would correspond to the position being effectively the same as that which was the case when the first energy was transduced could result in the resonance frequency of the transducer changing, which would require an adjustment to the transducer. Note also that in some exemplary embodiments, the effects of the position change can be compensated for via the use of software or signal processing techniques. Such movement would be within the ambit of a position of the transducer still being at least effectively the same as that which was the case when the first energy was transduced. Conversely, if the position of the transducer must be changed and/or a mechanical feature of the implantable component must be adjusted (e.g., the output arm lengthened, etc.), such results in the transducer having moved in a manner where the position of the transducer relative to the oval window the cochlea is no longer at least effectively the same as that which was the case when the first energy was transduced.

Note that the utilization of the oval window is but one example of a reference point. In an exemplary embodiment, any other structure of the recipient can be utilized, such as by way of example only and not by way of limitation, any point on any of the bones of the ossicles, any point on the tympanic membrane, any point on the portion of the cochlea facing the middle ear cavity, etc.

Figure 25:
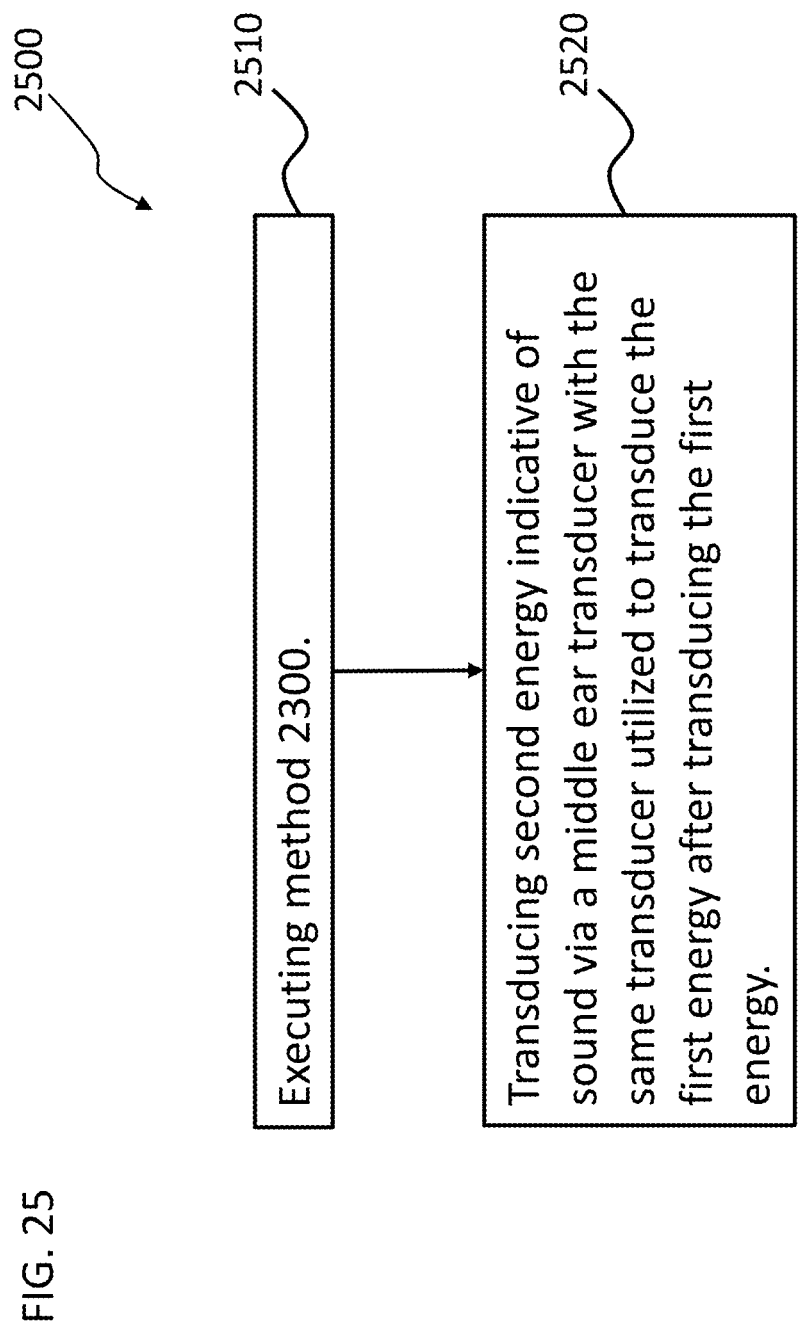

FIG. 25 presents another exemplary flowchart for an exemplary method, method 2500, which includes method action 2510, which includes executing method 2300 (or, in an alternate embodiment, only a portion of method 2300, such as only method action 2310). Again, as is the case with method 2400, method 2500 is executed in the aforementioned adolescent or pre-adolescent before completing full growth. Method 2500 further includes method action 2520, which includes transducing second energy indicative of sound via a middle ear transducer with the same transducer utilized to transduce the first energy after transducing the first energy. Here, there is no specified temporal period between the first and second transactions. (Again, it is noted that method 2300 and 2400, and methods 2500 and method 2600 detailed below, are methods that can be executed where the transducer is a microphone or some other form of sensor (any disclosure of a microphone herein corresponds to a disclosure of a sensor, including sensors that are different than microphones, and visa-versa, for some exemplary embodiments), or where the transducer is an actuator. It is also noted that the transducers herein can be electromagnetic transducers, piezoelectric transducers, or any other type of transducer that can enable the teachings detailed herein or otherwise can be used with the teachings detailed herein.

In method 2500, a point on bone of the recipient proximate the transducer (e.g., point A of FIGS. 17 and 18, mid-point 810 if such is proximate the transducer, or any other point) has moved at least W mm due to growth relative to the transducer, where W can be 0.25, 0.5, 0.75, 1, 1.25, 1.5, 1.75, 2, 2.25, 2.5, 2.75, 3, 3.5, 3.75, 4, 4.25, 4.5, 5, 5.5, 6, 6.5, 7, 7.5, 8, 9, or 10, or any value or range of values therebetween in 0.01 mm increments. In an exemplary embodiment, the position of the transducer relative to the oval window of the cochlea (or any other relative landmark in the middle ear, and, as is the case with all of the methods in at least some embodiment, any landmark that does not significantly grow relative to the growth associated with/that results in the movement of the aforementioned point) has moved no more than F during the time period from the first energy transduction to the second energy transduction, where F can be 0, 0.25, 0.5, 0.75, 1, 1.25, 1.5, 1.75, 2, 2.25, 2.5, 2.75, 3, 3.5, 3.75, 4, 4.25, 4.5, 5, 5.5, 6, 6.5, 7, 7.5, 8, 9, or 10, or any value or range of values therebetween in 0.01 mm increments.

Figure 25A:
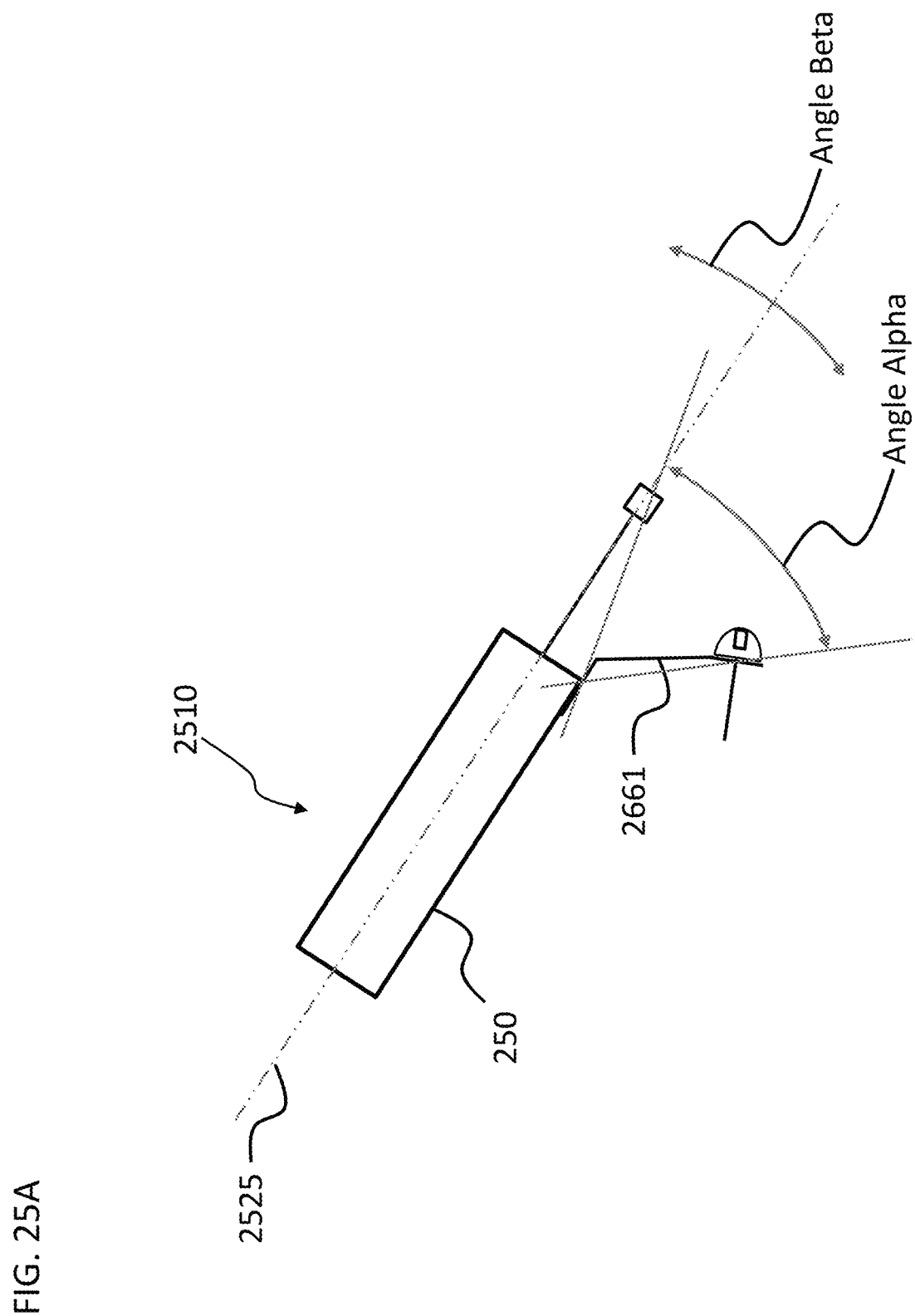

In an alternate embodiment of method 2500, the transducer is part of an assembly that is coupled to a first location of the recipient at a middle ear bone or at a window of the cochlea to enable the transduction of energy thereby. This is as opposed to the fixation structure which fixes the transducer to the middle ear cavity, which does not enable the transduction of energy. Indeed, in an exemplary embodiment of method 2500, consistent with the teachings above, the transducer is supported in the recipient via a fixation structure fixed at a second location of the recipient in the middle ear cavity. Further, in this exemplary method, a skull size has increased by at least U % due to growth from the first transduction to the second transduction, where U can be 10, 15, 20, 25, 30, 35, 40, 45, 50, 55, 60, 65, 70, 75, 80, 85, 90, 100, 120, 140, 160, 180, or 200 or more or any value or range of values therebetween in 1 increments. In this exemplary embodiment one or both of (i) a distance between the first location and the second location has not increased more than T percent or (ii) an angle between the first location and the second location with a vertex at a fixed point on the transducer where the fixation structure contacts a housing of the transducer has not increased more than alpha degrees (where alpha is depicted by way of example in FIG. 25A with respect to implanted assembly 2510). T can be 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 100, 110, 120, 130, 140 or 150 or any value or range of values therebetween in 0.1 increments, and alpha can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 degrees.

In an exemplary embodiment, instead of "i" and/or "ii" above, there is the feature that an angle between the longitudinal axis of the fixation arm 252 at the beginning of Q or prior to the growth, etc., or any of the above noted initial scenarios, and the longitudinal axis 2525 of the transducer (depicted as parallel and aligned in FIG. 25A, but in some embodiments, the axes do not align at the beginning of the temporal period owing to placement of the transducer and/or the location where the fixation arm 252 is attached to the middle ear structure) changes by no more than beta, where beta can be any of the values of alpha above. With respect to a fixation arm 252 that has a dog leg structure or the like, and thus potentially no definitive longitudinal axis, the pertinent axis would be the axis extending from the location where the fixation arm contacts the diaphragm to the location where the fixation arm is fixed to the middle ear structure.

Figure 26:
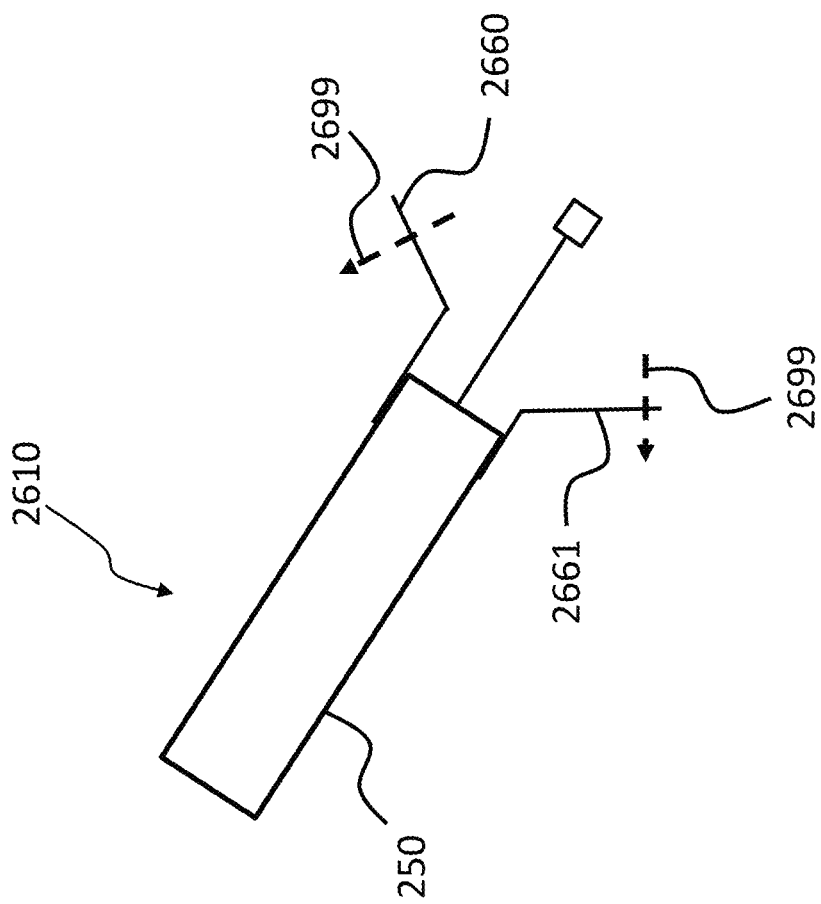

In an exemplary embodiment of one or more of the methods detailed above, the transducer is supported in the recipient via a fixation structure that applies compressive force in the middle ear cavity to fix the transducer in the recipient. In an exemplary embodiment, this is executed without adhesive between the fixation structure and the bone or other structure of the middle ear cavity and is executed without a bone screw or the like fixing the fixation structure to the bone or other structure the middle ear cavity. Indeed, in an exemplary embodiment, the transducer is only supported in the recipient via the compressive force. FIG. 26 conceptually depicts an exemplary embodiment of an implantable apparatus 2610, which includes fixation arms 2660 and 2661 (two point fixation—this embodiment can be utilized with three, four, five, six or more point fixation), which are configured and arranged such that when the implantable apparatus is implanted in the recipient, the arms 2660 and 2661 are compressed towards each other (as shown in FIG. 26), but the spring component/resilient nature of the fixation arms is such that the fixation arms apply a force in the direction of arrows 2699 against, in this embodiment, the respective wall portions of the middle ear cavity, thus fixing the implantable apparatus in the recipient. By rough analogy, this is analogous to a wedge anchor for anchoring a bolt or other fastener into concrete.

Figure 27:
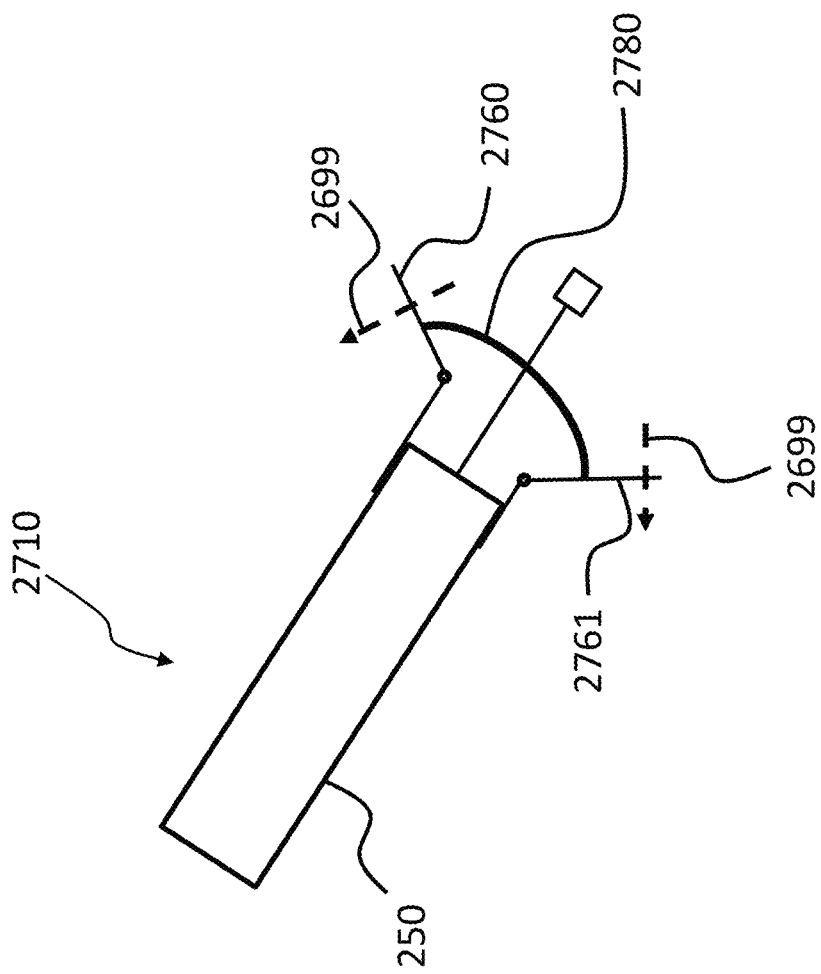

While the embodiment of FIG. 26 has been presented in terms of utilizing arms that have a spring feature associated there with, in an alternate embodiment, the arms could be plastically deformed to achieve the resulting compressive force and/or another component can be utilized to establish the compressive force. FIG. 27 depicts such an arrangement, where the implantable apparatus 2710 includes arms 2760 and 2761 that have hinge components, and thus the ends of the arms are free to articulate about the hinge, but spring 2780 provides a force on the arms to result in a compression force in the direction of arrows 2699. It is noted that while the embodiment of FIG. 27 depicts a spring in the form of 2780, in an alternate embodiment, spring 2780 can be a jack screw or other type of component. Indeed, element 2780 can be a scissor jack or the like, where, for example, element 2780 constitutes two arms that are scissored, and a component extends from the fulcrum to the transducer or another portion of the arms that is fixed relative to the transducer, which component pulls the element 2780 towards the transducer, and thus pushes the ends of the arms 2760 and 2761 in the direction of arrows 2699.

While the embodiments of FIGS. 26 and 27 depict the arms having flat surfaces which abide against the walls of the middle ear cavity, in an alternate embodiment, the arms can have studs or raised portions that focus the compressive force on a more limited area of the walls of the middle ear cavity.

In view of the above, in some embodiments, the fixation mechanism is configured to be fixed relative to the middle ear cavity solely via compressive forces of the middle ear cavity onto elastic portions of the fixation mechanism.

Note also that the embodiments of FIGS. 26 and 27 can be utilized in conjunction with bone spikes or the like, where the spikes are not as long and/or not threaded like the bone screws, but are configured to dig into the wall of the middle ear cavity. This can result in a less intrusive or otherwise invasive surgical procedure relative to the wall of the middle ear cavity (the spikes may not extend as deep as the comparable bone screws, may not have as large of a diameter as the comparable bone screws), and otherwise can enable a relatively faster installation process (the spikes "automatically" dig into the bone upon sufficient compression, as opposed to the need to first position the bone screws and then turn the bone screws with a surgical screwdriver or the like).

In some embodiments, the methods detailed herein are executed such that the transducer is supported in the recipient via a fixation structure that is glued to inner walls of the middle ear to fix the transducer in the recipient.

Figure 28:
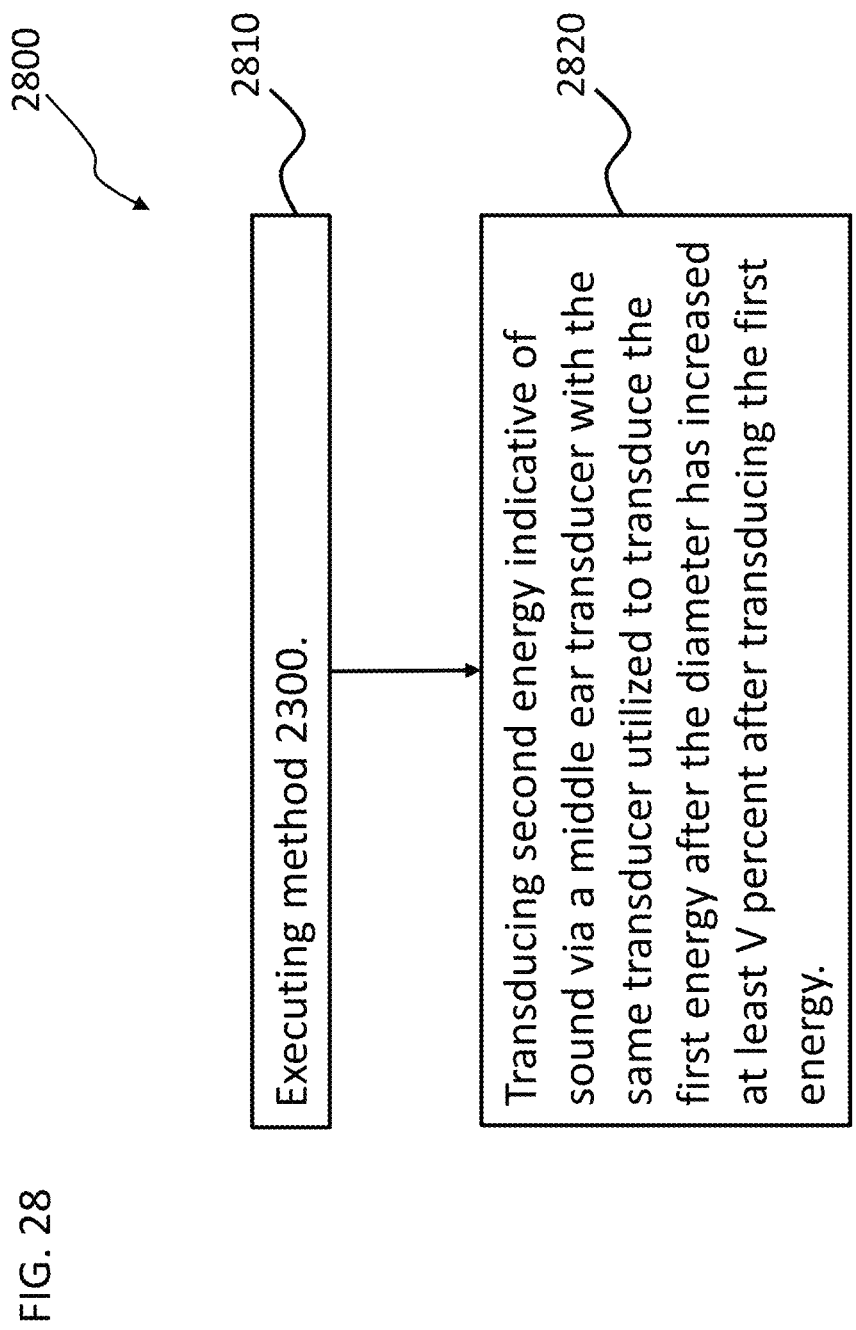
FIG. 28 presents an exemplary flowchart according to an exemplary embodiment.

FIG. 28 presents an alternate flowchart for an exemplary method, method 2800, which includes method action 2810, which includes executing method 2300, or at least a portion thereof, such as method action 2320. In this exemplary embodiment, the at least a portion of the transducer used to execute method action 2320 is located in an artificial passageway having a first diameter about the portion of the transducer when the first energy is transduced. In at least some exemplary embodiments, because the diameter of the passageway is constant along the whole length of the passageway, or at least most of passageway, this diameter is the diameter of the passageway that results from the boring action detailed above. In this exemplary embodiment, method 2800 includes method action 2820, which includes transducing second energy indicative of sound via a middle ear transducer with the same transducer utilized to transduce the first energy after the diameter has increased at least V percent after transducing the first energy, where V can be 5, 10, 15, 20, 25, 30, 35, 40, 45, 50, 55, 60, 65, 70, 75, 80, 85, 90, 100, 120, 140, 160, 180, or 200, or any value or range of values therebetween in 1 increments. As with some of the methods detailed above, no intervening surgery occurred between the first and the second energy transductions to relocate the transducer and/or no intervening mechanical adjustment of the transducer's position has occurred between the first and second energy transduction.

In some exemplary embodiments of the exemplary methods detailed above, the at least a portion of the transducer is located in an artificial passageway that has a first length from a beginning of the passageway to an end of the passageway, the end of the passageway opening in the middle ear cavity and a distance from a location in the recipient where the transducer is fixed to a location where the transducer is supported by a fixation structure (e.g., distance S of FIG. 22) is less than the first length, wherein the fixation structure extends between the two distances.

In some exemplary embodiments, the distance G of FIG. 17, which is the distance from the opening of the passageway 219 at the surface the mastoid bone to the closest portion of the transducer to the opening, is greater than D and/or N and/or S of FIG. 22. In some embodiments, G is 10, 15, 20, 25, 30, 35, 40, 45, 50, 55, 60, 65, 70, 75, 80, 85, 90, 95, 100, 125, 150, 175, 200, 225, 250, 275, 300, 350, 400, 450, or 500 or any value or range of values therebetween in 1% increments greater than one or more of D and/or N and/or S.

Figure 29:
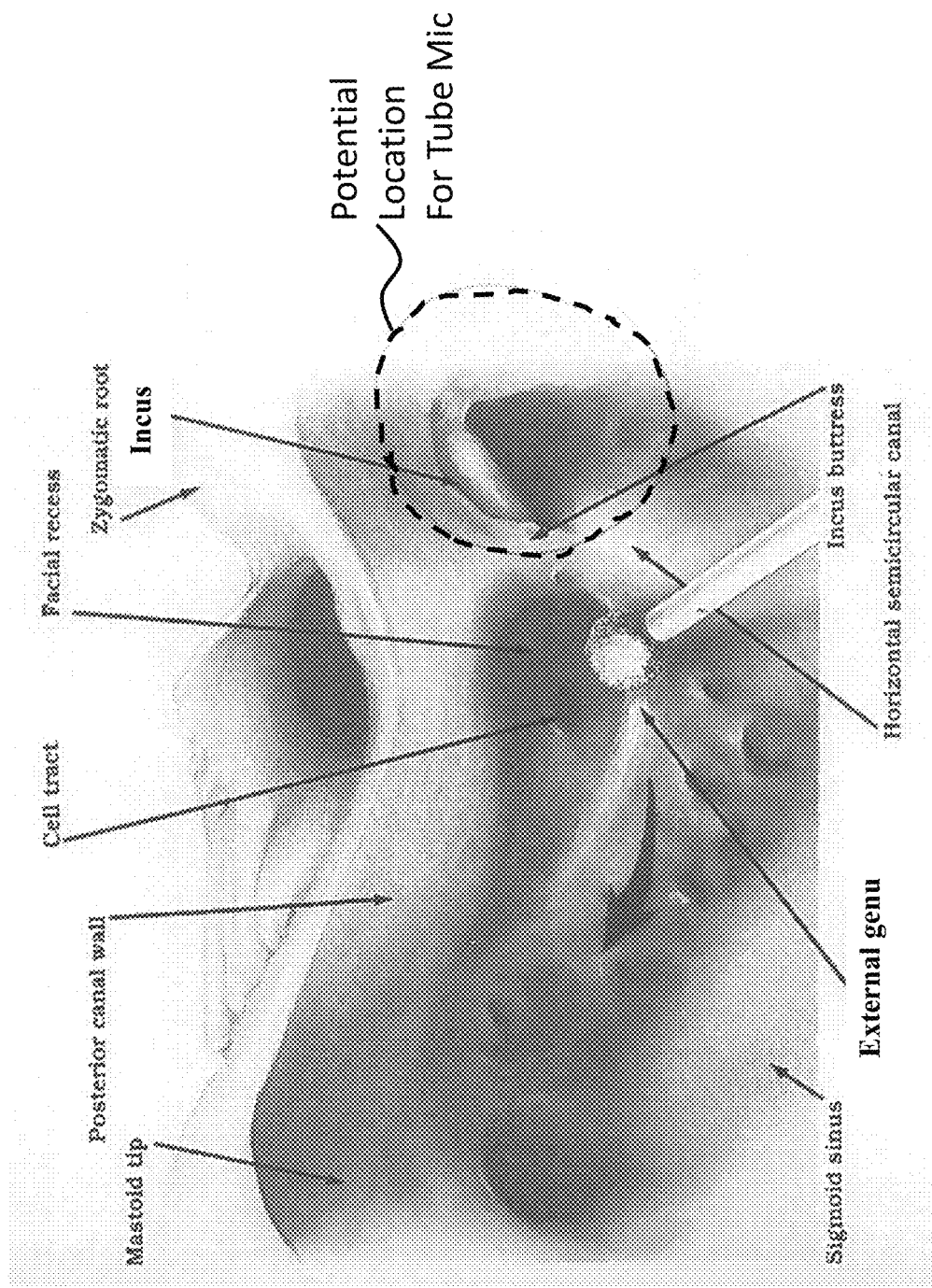
FIG. 29 presents a schematic depicting an exemplary location for the tube mic.

FIG. 29 depicts potential locations for the tube mic in embodiments that utilize such as the transducer.

In an exemplary embodiment, there is an implantable apparatus, comprising: an implantable transducer fixation mechanism, the fixation mechanism being configured to receive an implantable transducer, wherein the fixation mechanism is configured to be fixed to a wall of the middle ear cavity of the recipient, and the fixation mechanism is configured to locate the transducer at least partially outside the middle ear cavity. In an exemplary embodiment of the implantable apparatus as described above and/or below, the apparatus further comprises the transducer, wherein the transducer is a middle-ear actuator that includes a force output portion, wherein the fixation mechanism includes a fixation arm that extends away from the force output portion, and the fixation arm is configured to be secured to the recipient in the middle ear cavity of the recipient. In an exemplary embodiment of the implantable apparatus as described above and/or below, the apparatus further comprises the fixation mechanism is configured to be fixed relative to the middle ear cavity solely via compressive forces of the middle ear cavity onto elastic portions of the fixation mechanism.

In an exemplary embodiment, there is a method, comprising: obtaining access to a recipient; and fixing a transducer in a recipient such that the transducer is at least partially located outside a middle ear cavity by securing the transducer to structure of the recipient in the middle ear cavity. In an exemplary embodiment of this embodiment, the transducer is at least partially located in an artificial passageway, the artificial passageway extending through a temporal bone of the recipient upon the completion of the action of fixing the transducer. In an exemplary embodiment of the method just describe or others, upon completion of the action of fixation, the at least a portion of the transducer is supported in the artificial passageway via at least a quasi-cantilever regime. In an exemplary embodiment of the method just describe or others, the recipient is less than 13 years old and a portion of the recipient where the transducer is at least partially located is subject to growth movement relative to the transducer.

In an exemplary embodiment, there is an implantable apparatus, comprising: an implantable transducer fixation mechanism, the fixation mechanism being configured to receive an implantable transducer; and a middle ear transducer, wherein the middle ear transducer is incompatible with complete placement in a middle ear, wherein the implantable transducer fixation mechanism is a growing child compatible fixation mechanism. In an exemplary embodiment of this apparatus, the transducer includes a cylindrical component with an outer diameter of more than 3 mm and a length of more than 3 mm. In an exemplary embodiment of this exemplary embodiment, the fixation mechanism includes at least two fixation arms that extend away from the transducer to enable a two point fixation regime inside the middle ear cavity.

In an exemplary embodiment, there is a method, comprising: activating a middle ear transducer implanted in a recipient; and transducing first energy indicative of sound via the middle ear transducer for a first time after an implantation procedure of the transducer is fully completed, wherein the middle ear transducer is located at least partially outside the middle ear cavity, and the middle ear transducer is only fixed to structure inside the middle ear cavity. In an exemplary embodiment of this method, the transducer is supported in the recipient via a fixation structure that is spiked into inner walls of the middle ear to fix the transducer in the recipient.

It is noted that any disclosure of a device and/or system herein corresponds to a disclosure of a method of utilizing such device and/or system. It is further noted that any disclosure of a device and/or system herein corresponds to a disclosure of a method of manufacturing such device and/or system. It is further noted that any disclosure of a method action detailed herein corresponds to a disclosure of a device and/or system for executing that method action/a device and/or system having such functionality corresponding to the method action. It is also noted that any disclosure of a functionality of a device herein corresponds to a method including a method action corresponding to such functionality. Also, any disclosure of any manufacturing methods detailed herein corresponds to a disclosure of a device and/or system resulting from such manufacturing methods and/or a disclosure of a method of utilizing the resulting device and/or system.

Unless otherwise specified or otherwise not enabled by the art, any one or more teachings detailed herein with respect to one embodiment can be combined with one or more teachings of any other teaching detailed herein with respect to other embodiments.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An implantable apparatus, comprising:
    an implantable transducer fixation mechanism, the fixation mechanism being configured to receive an implantable transducer, wherein
    the fixation mechanism is configured to be fixed to a wall of a middle ear cavity of a recipient,
    the fixation mechanism is configured to locate the transducer at least partially outside the middle ear cavity, and
    at least one of:
        (i) the fixation mechanism is configured to extend from an artificial passageway that extends through a temporal bone into the middle ear cavity, and the artificial passageway has a cross-section that has a diameter value no greater than 18 mm at a location where the fixation mechanism is located;
        (ii) the fixation mechanism is integral with a housing of the transducer, and the fixation mechanism is configured such that a location where the fixation mechanism becomes integral with the housing is at least partially located outside the middle ear cavity when the fixation mechanism is secured to the wall; or
        (iii) the implantable apparatus includes the transducer, wherein the transducer is a tube microphone that includes a vibration input portion, wherein the fixation mechanism includes a fixation arm that extends away from the vibration input portion, the vibration input portion faces the fixation arm, and the fixation arm is configured to be secured to the recipient in the middle ear cavity of the recipient.

2. The implantable apparatus of claim 1, wherein:
the fixation mechanism is integral with the housing of the transducer; and
the fixation mechanism is configured such that the location where the fixation mechanism becomes integral with the housing is at least partially located outside the middle ear cavity when the fixation mechanism is secured to the wall.

3. The implantable apparatus of claim 1, wherein:
the fixation mechanism is configured to enable the transducer to move relative to a component of the fixation mechanism fixed to the wall, thereby enabling the transducer to be adjustably positioned at a location at least partially outside the middle ear cavity when the fixation mechanism is fixed to the wall.

4. The implantable apparatus of claim 1, wherein:
the fixation mechanism is configured to extend from the artificial passageway that extends through the temporal bone into the middle ear cavity.

5. The implantable apparatus of claim 4, wherein:
the cross-section is circular, and the diameter value is anywhere from 1 mm to 10 mm at the location where the fixation mechanism is located.

6. The implantable apparatus of claim 1, further comprising:
the transducer, wherein the transducer is the tube microphone that includes the vibration input portion, wherein
the fixation mechanism includes the fixation arm that extends away from the vibration input portion,
the vibration input portion faces the fixation arm, and
the fixation arm is configured to be secured to the recipient in the middle ear cavity of the recipient.

7. The implantable apparatus of claim 1, wherein:
the fixation mechanism is configured to provide at least three point fixation within the middle ear cavity.

8. A method, comprising:
obtaining access to a recipient; and
fixing a transducer in the recipient such that the transducer is at least partially located outside a middle ear cavity by securing the transducer to structure of the recipient in the middle ear cavity.

9. The method of claim 8, wherein:
the transducer is at least partially located in an artificial passageway, the artificial passageway extending through a temporal bone of the recipient upon a completion of the action of fixing the transducer.

10. The method of claim 9, wherein:
a fixation component is utilized to fix the transducer, wherein upon completion of the action of fixation, the fixation component extends from a wall of the middle ear cavity to the transducer so as to fix at least a portion of the transducer in the artificial passageway.

11. The method of claim 10, wherein:
upon completion of the action of fixation, no part of the fixation component or the transducer is fixed to a wall of the artificial passageway and no part of the fixation component or the transducer is fixed to an outer surface of the temporal bone.

12. The method of claim 10, wherein:
upon completion of the action of fixation, the transducer can be controllably moved in the artificial passageway.

13. The method of claim 9, wherein:
upon completion of the action of fixation, portions of the artificial passageway surrounding the transducer can move in a longitudinal direction relative to the transducer due to growth without causing the transducer to move.

14. The method of claim 8, wherein:
the recipient is in adolescence or pre-adolescence and a portion of the recipient where the transducer is at least partially located is subject to growth movement relative to the transducer.

15. The method of claim 8, further comprising:
attaching a working end of the transducer to a component that will result in fluid motion within a cochlea of an inner ear of the recipient upon actuation of the transducer.

16. An implantable apparatus, comprising:
an implantable transducer fixation mechanism, the implantable transducer fixation mechanism being configured to receive a middle ear transducer; and
the middle ear transducer, wherein the middle ear transducer is an implantable transducer and is incompatible with complete placement in a middle ear, wherein
the implantable transducer fixation mechanism is configured so that at least a portion of the implantable transducer fixation mechanism is located outside a middle ear cavity in a temporal bone when the implantable transducer fixation mechanism supports the middle ear transducer in the passageway, and
the implantable transducer fixation mechanism is configured to enable the temporal bone to grow as a recipient child grows to adulthood while accommodating growth of the recipient child into adulthood.

17. The implantable apparatus of claim 16, wherein:
the implantable transducer fixation mechanism includes a fixation arm that extends away from the middle ear transducer at an oblique angle relative to a longitudinal axis of the transducer.

18. The implantable apparatus of claim 16, wherein:
the implantable transducer fixation mechanism includes at least three fixation arms that extend away from the transducer to enable a three point fixation regime inside the middle ear cavity.

19. The implantable apparatus of claim 16, wherein:
the implantable transducer fixation mechanism is configured to enable the temporal bone to grow as the recipient child grows to adulthood while limiting a movement of a point on the implantable transducer fixation mechanism furthest away from the middle ear cavity and proximate the middle ear transducer and located outside the middle ear cavity when implanted in the recipient child to no more than 25% of relative movement of a nearest recipient structure to the point.

20. The implantable apparatus of claim 16, wherein:
the implantable transducer fixation mechanism is configured to enable the temporal bone to grow as the recipient child grows to adulthood while limiting a movement of a point on the implantable transducer fixation mechanism furthest away from the middle ear and proximate the middle ear transducer and located outside the middle ear cavity when implanted in a recipient child to no more than 15% of relative movement of a nearest nearest recipient structure to the point.

21. The implantable apparatus of claim 16, wherein:
the middle ear transducer is part of an assembly that is configured at a first connection location to be mechanically coupled to one of a middle ear bone or a window of a cochlea at a first connection point to enable mechanical energy transfer thereat;

the implantable transducer fixation mechanism is configured at a second connection location to be mechanically coupled to a wall of the middle ear to fix the implantable transducer fixation mechanism to the middle ear; and a shortest distance between the first connection point and the second connection point when the implantable apparatus is in free space and unrestrained is no more than about 5 mm.

22. The implantable apparatus of claim 16, wherein:

the implantable transducer fixation mechanism is configured to fix the middle ear transducer to the recipient child via fixation components only located in the middle ear.

23. A method, comprising:

activating a middle ear transducer implanted in a recipient; and transducing first energy indicative of sound via the middle ear transducer for a first time after an implantation procedure of the transducer is fully completed, wherein the middle ear transducer is located at least partially outside a middle ear cavity, and the middle ear transducer is only fixed to structure inside the middle ear cavity.

24. The method of claim 23, wherein:

the action of transducing first energy indicative of sound via the middle ear transducer is executed in an adolescent or a pre-adolescent before completing full growth; and the method further comprises:

transducing second energy indicative of sound via the middle ear transducer with the same middle ear transducer utilized to transduce the first energy 5 years after transducing the first energy, wherein a point on bone of the recipient proximate the transducer has moved significantly due to growth relative to the transducer since the first energy was transduced, the position of the middle ear transducer relative to the oval window of the cochlea is at least effectively the same as when the first energy was transduced, and no intervening surgery occurred between the first and the second energy transductions to relocate the transducer and/or no mechanical movement of the transducer has occurred to compensate for movement of the point on the bone.

25. The method of claim 23, wherein:

the action of transducing energy indicative of sound via the middle ear transducer is executed in an adolescent or a pre-adolescent before completing full growth; and the method further comprises:

transducing second energy indicative of sound via the middle ear transducer with the same middle ear transducer utilized to transduce the first energy after transducing the first energy, wherein a point on bone of the recipient proximate the transducer has moved at least 2 mm due to growth relative to the transducer, and the position of the middle ear transducer relative to the oval window of the cochlea has moved no more than 1 mm during the time period from the first energy transduction to the second energy transduction.

26. The method of claim 23, wherein:

the action of transducing energy indicative of sound via the middle ear transducer is executed in an adolescent or a pre-adolescent before completing full growth;

the middle ear transducer is part of an assembly that is coupled to a first location of the recipient at a middle ear bone or at a window of the cochlea to enable the transduction of energy thereby;

the middle ear transducer is supported in the recipient via a fixation structure fixed at a second location of the recipient in the middle ear cavity; and the method further comprises:

transducing second energy indicative of sound via the middle ear transducer with the same middle ear transducer utilized to transduce the first energy after transducing the first energy, wherein a skull size has increased by at least 30% due to growth from the first transduction to the second transduction, and at least one of:

a distance between the first location and the second location has not increased more than 30 percent; or an angle between the first location and the second location with a vertex at a fixed point on the middle ear transducer where the fixation structure contacts a housing of the transducer has not increased more than 30 degrees.

27. The method of claim 23, wherein:

the transducer is supported in the recipient via a fixation structure that applies compressive force in the middle ear cavity to fix the transducer in the recipient.

28. The method of claim 23, wherein:

the transducer is supported in the recipient via a fixation structure that is glued to inner walls of the middle ear cavity to fix the transducer in the recipient.

29. The method of claim 23, wherein:

at least a portion of the middle ear transducer is located in an artificial passageway having a first diameter about the at least a portion of the middle ear transducer that is located in the artificial passageway when the first energy is transduced; and the method further comprises:

transducing second energy indicative of sound via the middle ear transducer with the same middle ear transducer utilized to transduce the first energy after the diameter has increased at least 50 percent after transducing the first energy, wherein no intervening surgery occurred between the first and the second energy transductions to relocate the transducer.

30. The method of claim 23, wherein:

at least a portion of the middle ear transducer is located in an artificial passageway that has a first length from a beginning of the passageway to an end of the passageway, the end of the passageway opening into the middle ear cavity; and a distance from a location in the recipient where the middle ear transducer is fixed via a fixation structure to a location where the middle ear transducer is connected to the fixation structure is less than the first length, wherein the fixation structure extends between the two locations.

* * * * *